United States Patent
Eilbert et al.

(10) Patent No.: US 8,155,272 B2
(45) Date of Patent: Apr. 10, 2012

(54) METHODS AND APPARATUS FOR E-BEAM SCANNING

(75) Inventors: Richard Franklin Eilbert, Lincoln, MA (US); Boris Oreper, Newton, MA (US); Nikolay Rolshud, Winchester, MA (US)

(73) Assignee: L-3 Communications Security and Detection Systems Inc., Woburn, MA (US)

( * ) Notice: Subject to any disclaimer, the term of this patent is extended or adjusted under 35 U.S.C. 154(b) by 347 days.

(21) Appl. No.: 12/191,587

(22) Filed: Aug. 14, 2008

(65) Prior Publication Data

US 2010/0316188 A1     Dec. 16, 2010

Related U.S. Application Data

(63) Continuation of application No. 11/481,322, filed on Jul. 5, 2006, now Pat. No. 7,428,297.

(60) Provisional application No. 60/696,669, filed on Jul. 5, 2005.

(51) Int. Cl.
*H01J 35/06* (2006.01)
*H01J 35/30* (2006.01)
*G01N 23/083* (2006.01)

(52) U.S. Cl. ............... 378/134; 378/9; 378/10; 378/92; 378/137

(58) Field of Classification Search ............... 378/9, 10, 378/57, 92, 98.6, 113, 124, 134, 137
See application file for complete search history.

(56) References Cited

U.S. PATENT DOCUMENTS

| | | | |
|---|---|---|---|
| 4,274,005 A * | 6/1981 | Yamamura et al. ............... 378/9 |
| 4,352,021 A | 9/1982 | Boyd et al. | |
| 4,685,118 A * | 8/1987 | Furbee et al. ................. 378/114 |
| 5,172,401 A * | 12/1992 | Asari et al. ...................... 378/10 |
| 5,490,193 A * | 2/1996 | Kuroda et al. .................. 378/10 |
| 5,491,734 A | 2/1996 | Boyd et al. | |
| 5,548,630 A * | 8/1996 | Hell et al. ...................... 378/137 |
| 5,995,586 A * | 11/1999 | Jahnke .......................... 378/137 |
| 6,018,562 A * | 1/2000 | Willson .............................. 378/9 |
| 6,088,423 A * | 7/2000 | Krug et al. ...................... 378/57 |
| 6,236,709 B1 * | 5/2001 | Perry et al. ...................... 378/57 |
| 6,453,003 B1 * | 9/2002 | Springer et al. ................. 378/57 |
| 6,542,574 B2 * | 4/2003 | Grodzins ........................ 378/57 |
| 6,628,745 B1 | 9/2003 | Annis et al. | |
| 6,735,271 B1 | 5/2004 | Rand et al. | |
| 6,895,072 B2 * | 5/2005 | Schrock et al. ................. 378/57 |
| 6,993,111 B1 * | 1/2006 | Annis ............................. 378/57 |

(Continued)

FOREIGN PATENT DOCUMENTS

WO        WO 02/43565 A1        6/2002

*Primary Examiner* — Edward Glick
*Assistant Examiner* — Thomas R Artman
(74) *Attorney, Agent, or Firm* — Wolf, Greenfield & Sacks, P.C.

(57) ABSTRACT

In one aspect, an x-ray scanning device is provided. The x-ray scanning device comprises a target adapted to convert electron-beam (e-beam) energy into x-ray energy, a detector array positioned to detect at least some x-rays emitted from the target, and a conveyer mechanism adapted to convey items to be inspected through an inspection region formed by the target and the detector array, wherein the target and the detector array are rotated out of alignment with each other such that x-rays emitted from the target impinge on diametrically positioned detectors of the detector array without passing through near-side detectors of the detector array.

17 Claims, 38 Drawing Sheets

U.S. PATENT DOCUMENTS

| | | |
|---|---|---|
| 7,023,950 B1 | 4/2006 | Annis |
| 7,203,269 B2 * | 4/2007 | Huber et al. .................... 378/10 |
| 7,233,644 B1 * | 6/2007 | Bendahan et al. ............. 378/57 |
| 7,333,588 B2 * | 2/2008 | Mistretta et al. ............... 378/10 |
| 7,428,297 B2 * | 9/2008 | Eilbert ......................... 378/134 |
| 7,643,606 B2 * | 1/2010 | Popescu ......................... 378/10 |
| 2003/0231739 A1 * | 12/2003 | Rosner .......................... 378/57 |
| 2005/0058242 A1 | 3/2005 | Peschmann |

* cited by examiner

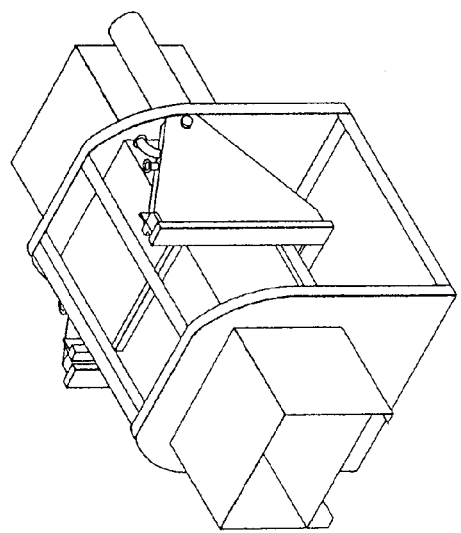
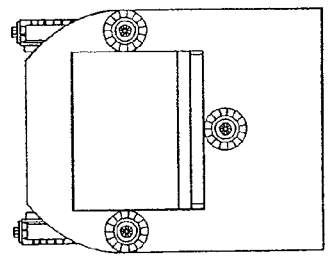
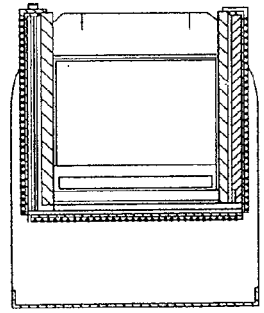
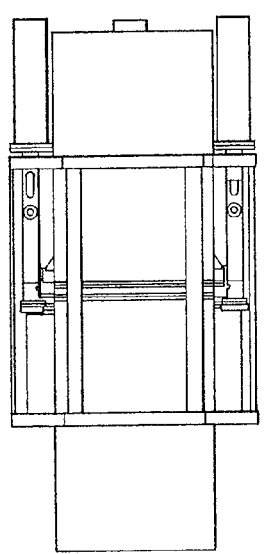
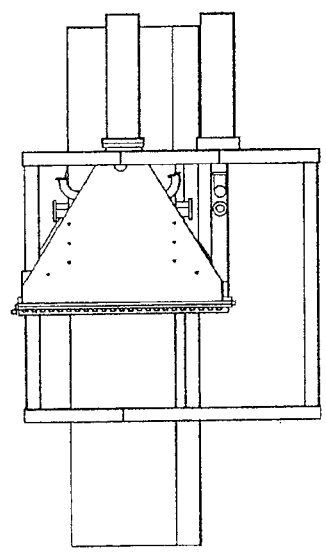
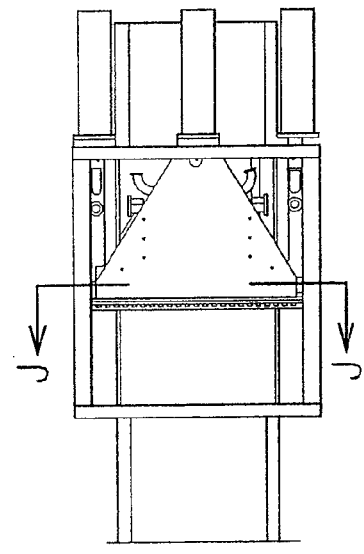
FIG. 15

METHODS AND APPARATUS FOR E-BEAM SCANNING

RELATED APPLICATION

This application is a continuation of U.S. application Ser. No. 11/481,322, entitled "Methods and Apparatus for E-Beam Scanning," filed on Jul. 5, 2006, which claims priority under 35 U.S.C. §119(e) to U.S. Provisional Application Ser. No. 60/696,669, entitled "Methods and Apparatus for E-beam Scanning," filed on Jul. 5, 2005, each of which is herein incorporated by reference in its entirety.

FIELD OF THE INVENTION

The invention relates to X-ray scanning systems that generate X-rays by directing one or more electron beams (e-beams) at a target responsive to the e-beam.

BACKGROUND OF THE INVENTION

X-ray imaging technology has been employed in a wide range of applications from medical imaging to detection of unauthorized objects or materials in baggage, cargo or other containers generally opaque to the human eye. X-ray imaging typically includes passing high energy radiation (i.e., X-rays) through an object to be imaged. X-rays from a source passing through the object interact with the internal structures of the object and are altered according to various characteristics of the material (e.g., transmission, scattering and diffraction characteristics, etc.) in which the X-rays encounter. By measuring changes (e.g., attenuation, energy spectrum, scatter angle, etc.) in the X-ray radiation that exits the object, information related to characteristics of the material such as density, atomic structure and/or atomic number, etc., may be obtained.

Many X-ray scanning systems employ electron beam (e-beam) technology to generate X-rays that penetrate an object of interest to investigate the object's properties. In e-beam technology, an e-beam is directed to impinge on the surface of a target responsive to the e-beam. The target may be formed from, for example, tungsten, molybdenum, gold, metal plated, or other material that emits X-rays in response to an electron beam impinging on its surface. For example, the target may be a material that converts energy in the e-beam into relatively high energy photons, emitted from the target essentially in the $4\pi$ directions. The released energy may be shaped or collimated by blocking selected portions of the X-rays emitted from the target using any of various radiation absorbing material (such as lead). For example, the X-ray may be collimated to form a cone beam, a fan beam, a pencil beam or any other X-ray beam having generally desired characteristics. The collimated X-rays may then pass into an inspection region to penetrate an object of interest to ascertain one or more characteristics of the object.

An electron beam may be generated, for example, from an electron source, the electrons being accelerated and directed as desired along the surface of the target. For example, a generated e-beam may be directed magnetically by bending the beam using one or more magnetic coils, herein referred to as steering coils. In general, the e-beam propagates in a vacuum chamber until the e-beam impinges on the target. Various methods (e.g., bending an electron beam using one or more magnets) of providing an e-beam along a desired path over a surface of the target are well known in the art.

To measure X-ray radiation penetrating an object to be imaged, an array of detectors responsive to X-ray radiation typically is arranged about the object being imaged. Each detector in the array responds to X-rays impinging on its surface to provide a radiograph or view indicative of the total absorption (i.e., attenuation) incurred by material substantially in a line between the X-ray source and a detector in the array. The term "X-ray source" refers generally to an origin or origins of X-ray radiation. In e-beam technology, the X-ray source is typically the locations or points at which the e-beam impinges on the target, thus emitting X-rays from those locations in response to the e-beam. The X-ray source and detector array may be moved relative to one another to obtain a number of views of the object at different angles.

Conventional X-ray systems establish a circular relationship between X-ray source and detector. For example, an X-ray source and detector pair may be rotated along a circular path such that rays between the source and detector intersect at a common point (e.g., the center of the circular path). Alternatively, a circular array of detectors may be provided and a source may be rotated about a portion of a circular path (e.g., by providing an e-beam along a circular scanning path). X-ray systems having a circular geometry typically arrange detectors (or detector locations) equidistant from a common point. To generate X-rays that penetrate an inspection region over a number of different viewing angles (e.g., over 180°), a circular target arranged substantially concentric to and about the detectors is often employed. An e-beam is then typically directed generally in a line through the center point and then deflected such that the e-beam impinges on the target along a circular path. The resulting X-rays then penetrate the object of interest at a desired number of angles or views.

SUMMARY OF INVENTION

One embodiment according to the present invention includes an x-ray scanning device comprising a target adapted to convert electron beam (e-beam) energy into x-ray energy, the target including a first substantially linear portion, a second substantially linear portion, and a third substantially linear portion, the second substantially linear portion and the third substantially linear portions being arranged substantially perpendicular to the first substantially linear portion and substantially parallel to each other to form a first plane, an array of detectors adapted to detect x-ray radiation emitted from the target and passing through an inspection region, the array of detectors including a first detector array positioned substantially diametric to the first substantially linear portion, a second detector array positioned substantially diametric to the second substantially linear portion, and a third detector array positioned substantially diametric to the third substantially linear portion to form a second plane, wherein the first plane and the second plane intersect and are rotated with respect to one another such that the first plane and the second plane are not co-planar, the rotation sufficient such that at least some of the x-ray radiation emitted from the second substantially linear portion passing through the inspection region impinges on the second detector array without passing through the third detector array, and at least some of the x-ray radiation emitted from the third substantially linear portion passing through the inspection region impinges on the third detector array without passing through the second detector array.

Another embodiment according to the present invention includes an x-ray scanning device comprising a substantially rectangular shaped target adapted to convert electron-beam (e-beam) energy into x-ray energy, the target forming a first plane through which objects being inspected are intended to pass, a substantially rectangular shaped detector array positioned diametric to the substantially rectangular shaped target to detect at least some x-rays emitted from the target, the detector array forming a second plane through which the objects being inspected are intended to pass, the second plane dividing the X-ray scanning device into a first side and a second side, a conveyer mechanism adapted to convey the objects to be inspected through the first plane and the second plane in a first direction from the first side to the second side, a first e-beam generator positioned on the first side and adapted to generate a first e-beam to impinge on a first portion of the target along a first scanning path, and a second e-beam generator positioned on the second side and adapted to generate a second e-beam to impinge on a second portion of the target along a second scanning path.

Another embodiment according to the present invention includes an x-ray scanning device comprising a target adapted to convert electron-beam (e-beam) energy into x-ray energy, a detector array positioned to detect at least some x-rays emitted from the target, and a conveyer mechanism adapted to convey items to be inspected through an inspection region formed by the target and the detector array, wherein the target and the detector array are rotated out of alignment with each other such that x-rays emitted from the target impinge on diametrically positioned detectors of the detector array without passing through near-side detectors of the detector array.

Another embodiment according to the present invention includes a method of transitioning current generated by a power supply to operate a first electron beam (e-beam) generator and a second e-beam generator each adapted to provide a e-beam to impinge on respective portions of a target in an x-ray detection system, the target adapted to convert e-beam energy into x-ray energy, the method comprising acts of during a first interval, providing a first predetermined current to the operate the first e-beam generator, during the first interval, providing no current to the second e-beam generator, during a second interval, providing a decreasing amount of current to the first e-beam generator, during the second interval, providing an increasing amount of current to the second e-beam generator, during a third interval, providing a second predetermined amount of current to operate the second e-beam generator, and during the third interval, providing no current to the second e-beam generator.

Another embodiment according to the present invention includes a power supply comprising a power source adapted to operate a first electron beam (e-beam) generator and a second e-beam generator, and a controller adapted to control the power source such that, during a first interval, the power source provides a first predetermined current to operate the first e-beam generator and provides no current to the second e-beam generator, and during a second interval, the power source provides a decreasing amount of current to the first e-beam generator and provides an increasing amount of current to the second e-beam generator, and during a third interval, the power source provides a second predetermined amount of current to operate the second e-beam generator and provides no current to the first e-beam generator.

BRIEF DESCRIPTION OF THE DRAWINGS

FIGS. 8-16 illustrate various portions of an x-ray scanning system using dual electron beam generators, in accordance with various embodiments of the present invention;

DETAILED DESCRIPTION

Figure 1:
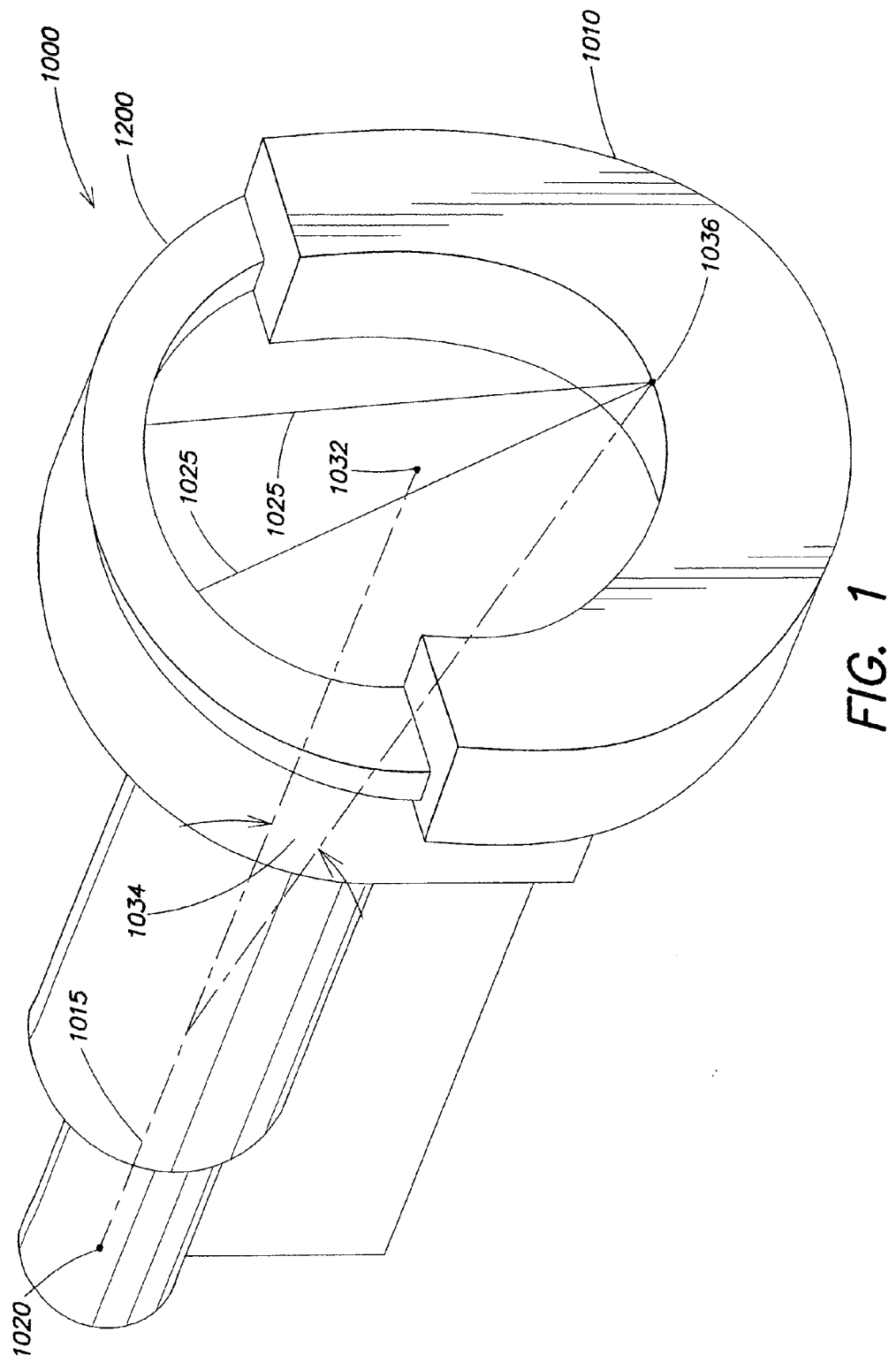
FIG. 1 illustrates a conventional circular geometry x-ray scanning system using e-beam technology.

As discussed above, conventional X-ray scanning systems employ a circular geometry between detector and X-ray source. In particular, the target and detector array have generally circular shapes. FIG. 1 illustrates schematically an X-ray scanning system employing e-beam technology in a circular geometry. X-ray scanning system 1000 includes an essentially circular target 1010 that responds to an impinging e-beam 1015 by emitting X-rays 1025 and an essentially circular array 1200 of detectors responsive to the radiation.

E-beam 1015 emanates from an e-beam source point 1020, for example, from an electron gun and is directed essentially along a longitudinal axis that penetrates a center point 1032 of the detector array (or target). One or more magnetic coils (not shown) deflect the e-beam from the longitudinal axis at a deflection angle 1034 so that the e-beam impinges on target 1010, for example, at location 1036 on the target. The resulting X-rays then penetrate an inspection region and impinge on the detector array. The X-ray scanning system may then be rotated in a number of ways such that the e-beam impinges at different locations on the target to form a scanning path along the target. As the e-beam is directed along a circular arc of the target, the resulting X-rays penetrate the inspection regions at different angles to provide different projections or views of an object positioned within the inspection region. Other circular geometry systems and methods related to e-beam scanning are described in U.S. Pat. No. 5,491,734 ('734) to Boyd et al., U.S. Pat. No. 4,352,021 ('021) to Boyd et al., and U.S. Pat. No. 6,735,271 ('271) to Rand et al., all of which are incorporated herein by reference in their entirety.

Various technical constraints, including the expense of the steering coils and characteristics of bending the e-beam limit the amount the e-beam can be practicably deflected. That is, design specifications may be deflection angle limited. Accordingly, the distance between an e-beam source and the target is often extended so that deflection angle constraints can be met, while still accommodating a particular detector array circumference. For example, the distance between e-beam source point 1020 and center point 1032 may be increased so that a smaller deflection angle is sufficient to allow the e-beam to impinge on target 1010. However, the vacuum tubes and the corresponding apparatus needed to enclose the path of the e-beam are relatively expensive and bulky. In addition, the extended vacuum region has relatively long field-free paths between the e-beam source point and the target, which require more extensive shielding and may be susceptible to stray electromagnetic (EM) fields. As a result, such systems are more costly to manufacture and more cumbersome to deploy due to the increased footprint, shielding requirements, etc.

Applicant has appreciated that arbitrary, and more particularly, non-circular geometries offer a number of benefits with respect to the flexibility of the design and may facilitate more compact and inexpensive X-ray detection systems. Applicant has identified and developed various e-beam techniques for use in arbitrary geometry systems that facilitate relatively inexpensive, compact and efficient X-ray detections systems.

In one embodiment according to the present invention, an X-ray scanning system is provided wherein X-rays are generated by directing an e-beam along a target via a scanning path that includes at least one substantially circular portion and at least one non-circular portion. One exemplary system includes a scanning path having a plurality of substantially linear portions and a plurality of substantially circular portions. For example, the scanning path may traverse a substantially rectangular U-shaped target formed from three substantially linear segments connected by substantially circular segments.

In another embodiment according to the present invention, an X-ray scanning system having a target that converts energy in an e-beam to X-ray energy is provided as a plurality of segments. In one exemplary configuration, the target comprises at least one substantially circular segment and at least one substantially linear segment. In some embodiments, the plurality of segments are provided continuously. In other embodiments, at least one of the plurality of segments is provided discontinuous with at least one other segment. For example, each segment may be offset in a direction parallel to the direction of conveyance of an item being inspected by the X-ray scanning system.

In another embodiment according to the present invention, an X-ray scanning system is provided wherein X-rays are generated by directing an e-beam along a target responsive to the e-beam at a variable scan rate. In one exemplary configuration, the e-beam traverses the target according to a scanning schedule that varies the scan rate to synchronize the scanning with a conveying apparatus such that a single traversal of the target generates X-rays that penetrate substantially the same cross-section of the item being scanned. In another exemplary configuration, the e-beam traverses the target according to a scanning schedule that varies the scan rate to generate X-rays having substantially similar penetration angles with respect to a center point of the inspection area of the X-ray scanning system.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention may be used alone or in any combination and are limited to the combinations illustrated in the specific embodiments described below.

Figure 2:
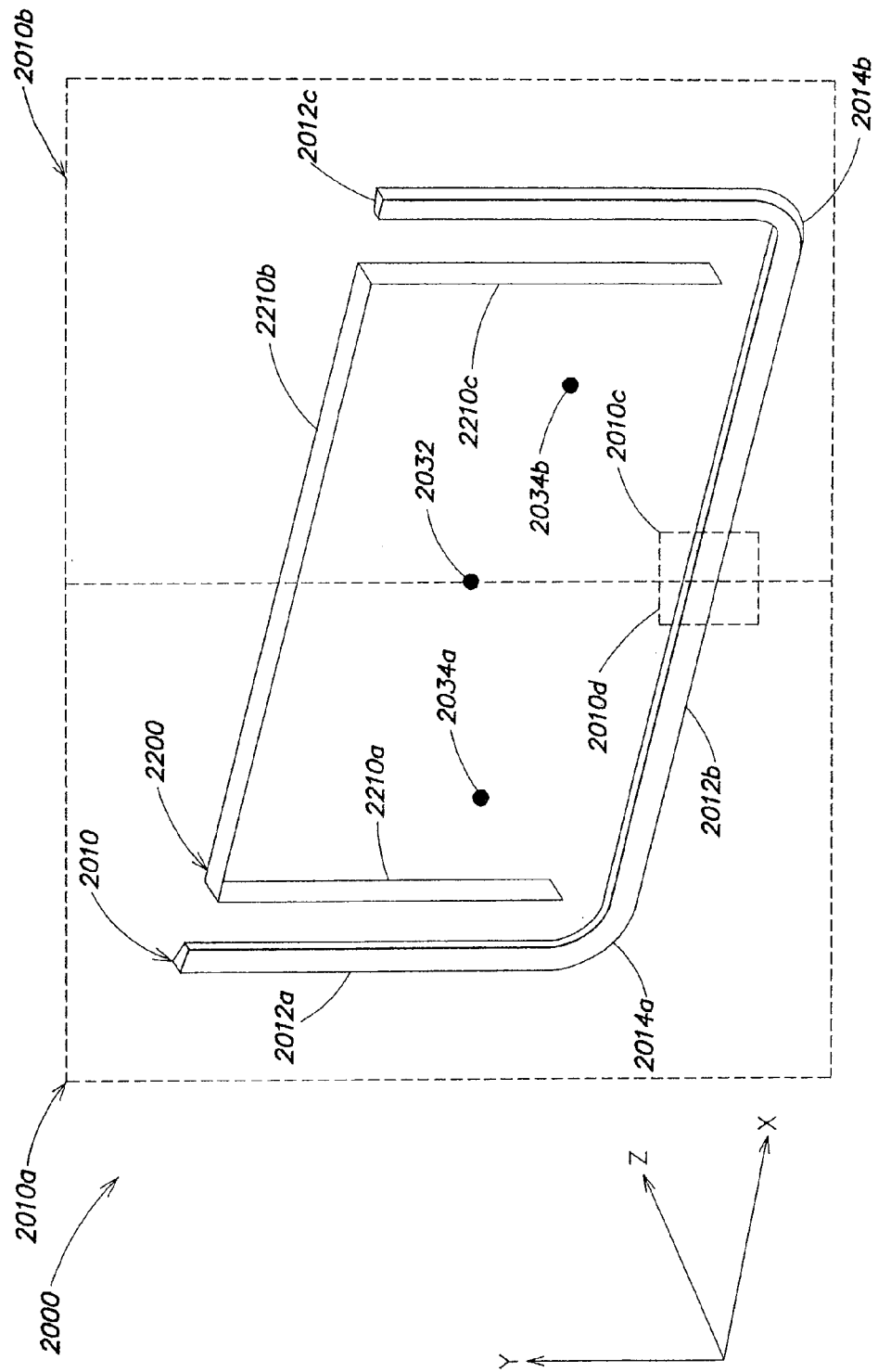
FIG. 2 illustrates an arbitrary geometry target and detector array using e-beam technology, in accordance with one embodiment of the present invention.

FIG. 2 illustrates portions of an X-ray scanning system, in accordance with one embodiment of the present invention. X-ray scanning system 2000 includes a non-circular detector array 2200. In particular, detector array 2200 is generally shaped as a rectangular U, sometimes referred to as goal posts, or staple-shaped, comprising substantially linear segments 2210a, 2210b and 2210c. The U-shaped geometry is merely exemplary of an arbitrary geometry array, which as the name suggests, may take on any shape, as the aspects of the invention are not limited in this respect. The various segments of the detector array may be continuous or they may be staggered, for example, along the z-axis, as described in further detail below. To irradiate the detector array 2200, a target 2010 that generally mimics the shape of detector array 2200 is positioned concentrically and diametrically from the detector array and operates as the e-beam anode.

The term "diametric" refers herein to positioning of a target and detector array in an opposing arrangement such that diametric portions of the detector array and target are generally facing one another such that x-rays emitted from the portions of the target impinge on the diametrically arranged portions of the detector array. Target 2010 includes substantially linear segments 2012a, 2012b, and 2012c and circular arc segments 2014a and 2014b. Accordingly, linear segment 2210c of the detector array is arranged diametrically to linear segment 2012a because the x-ray sensitive regions of the detectors on segment 2210c are facing target segment 2012a. Similarly, segments 2010b and 2010c of the detector array are arranged diametrically to circular segment 2014a of the target. As discussed above, target 2010 may be formed from any material that converts energy from an impinging e-beam into X-rays, such as tungsten, molybdenum, etc.

To minimize the deflection angle without unduly compromising the size of the inspection area, Applicant has appreciated that multiple e-beam generators, also referred to as electron guns, may be used. In addition, if the required deflection angle may be reduced for a given size target, then, rather than reducing the deflection angle, the same actual deflection angle may be used and the distance between the steering coils and the target may be reduced, as discussed in further detail below. This reduction in distance allows the vacuum tubes through which the e-beams travel after leaving the steering coils to be made smaller, substantially reducing both the cost and bulk of the resulting inspection system.

For example, a first electron gun may be deployed to scan portion 2010a of target 2010 and a second electron gun may be deployed to scan portion 2010b. In one embodiment, each electron gun scans substantially half of the target, and in a sequential fashion. By positioning the electron gun pair to scan substantially half of the array, the deflection angles for each gun may be reduced. For example, the electron guns may be positioned such that the e-beam would impinge somewhere along the respective target in the absence of deflection forces, rather than passing through, for example, a center point of the inspection region.

Alternatively, the electron beams, in the absence of deflection forces, may pass through points closer to respective portions of the target, rather than passing through the center point, or other points generally equidistant from various points along the target. For example, rather than having a single electron gun positioned such that the generated e-beam, in the absence of deflection forces, passes through a center points 2032 (as shown in FIG. 2), a pair of electron guns may be positioned such that their e-beams, in the absence of deflection forces, pass through points 2034a and 2034b, respectively. Multiple e-beam generators may be used in numerous configurations to reduce the required deflection angle and/or reduce vacuum tube sizes, as discussed in further detail below.

Figure 29:
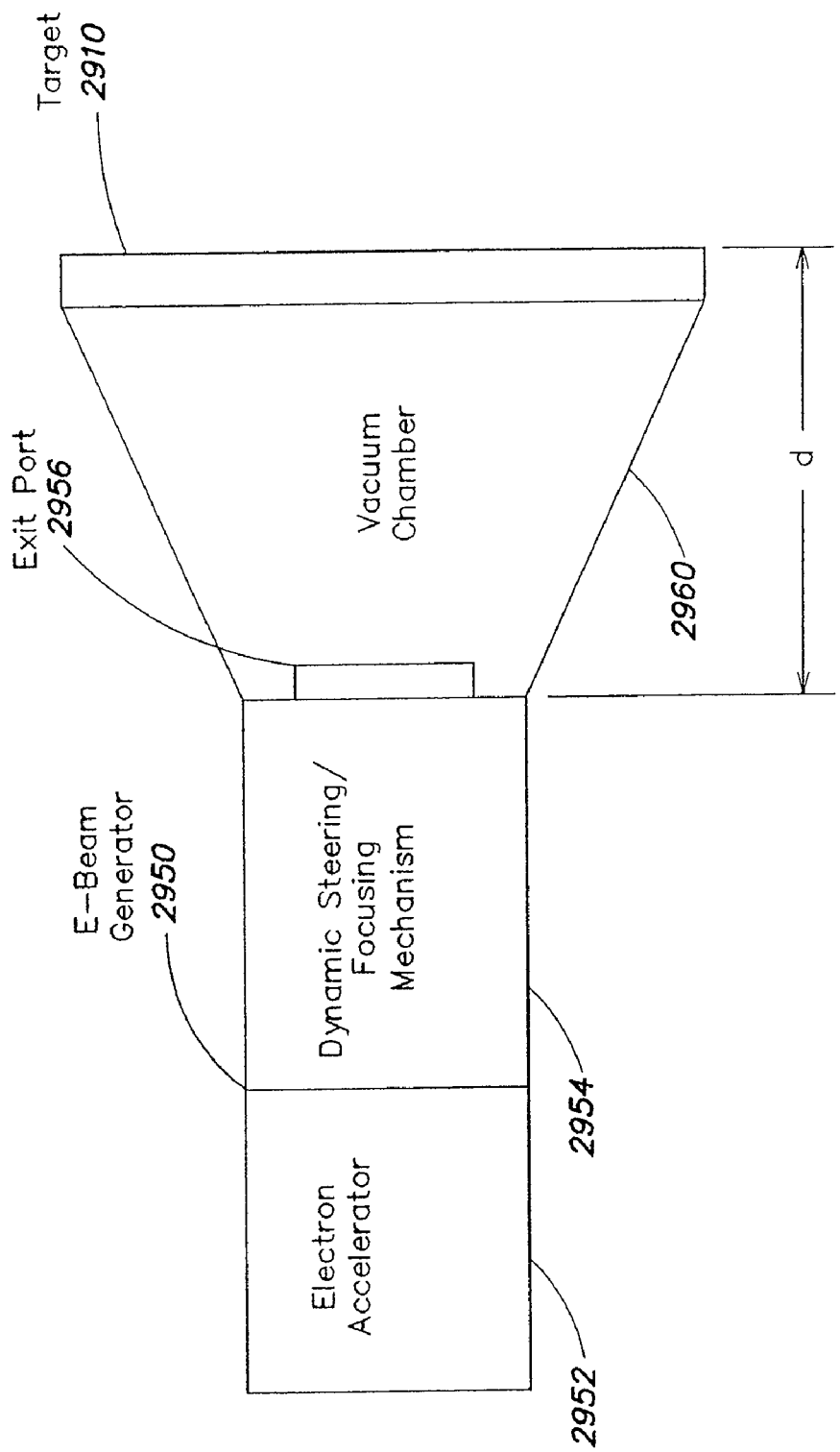
FIG. 29 illustrates an electron beam generator, in accordance with one embodiment of the present invention.

FIG. 29 illustrates an e-beam generator adapted to sweep an e-beam along a target to generate X-rays used to inspect objects of interest. The e-beam generator includes an electron accelerator 2952 adapted to accelerate electrons to an appropriate velocity to create an electron beam suitable for impinging on the target. Various electron/particle accelerators are well known in the art. After the electrons have been suitably accelerated, the electrons may be directed into dynamic steering/focusing mechanism 2954, referred to hereinafter as the steering mechanism. The steering mechanism is configured to bend the path of the electron beam (e.g., using magnetic steering coils) such that the electron beam impinges on target 2910 along a desired scanning path (e.g., from top to bottom of the target). The steering mechanism may also implement focusing components to focus the electrons into a generally desirable shaped beam having a suitable focal point. The electron accelerator and the steering mechanism is collectively referred to as the e-beam generator 2950 or electron gun, which, unless specifically stated otherwise are synonymous terms.

After the e-beam exits the steering mechanism through the exit port 2956, the e-beam propagates through vacuum tube 2960 to impinge on target 2910. Vacuum tube 2960 is generally a relatively expensive and bulky component. The larger the vacuum tube, the more expensive and bulky the x-ray scanning system becomes. The size of the vacuum tube is related to the distance between the exit port and the target, which is in turn related to the necessary deflection angle. Applicant has appreciated that by using multiple e-beam generators, the distance between the steering mechanism (e.g., the distal end of the e-beam generator) and the target may be reduced, thus reducing the size of the vacuum tube, facilitating a less expensive x-ray scanning system having a smaller footprint.

Figure 30A:
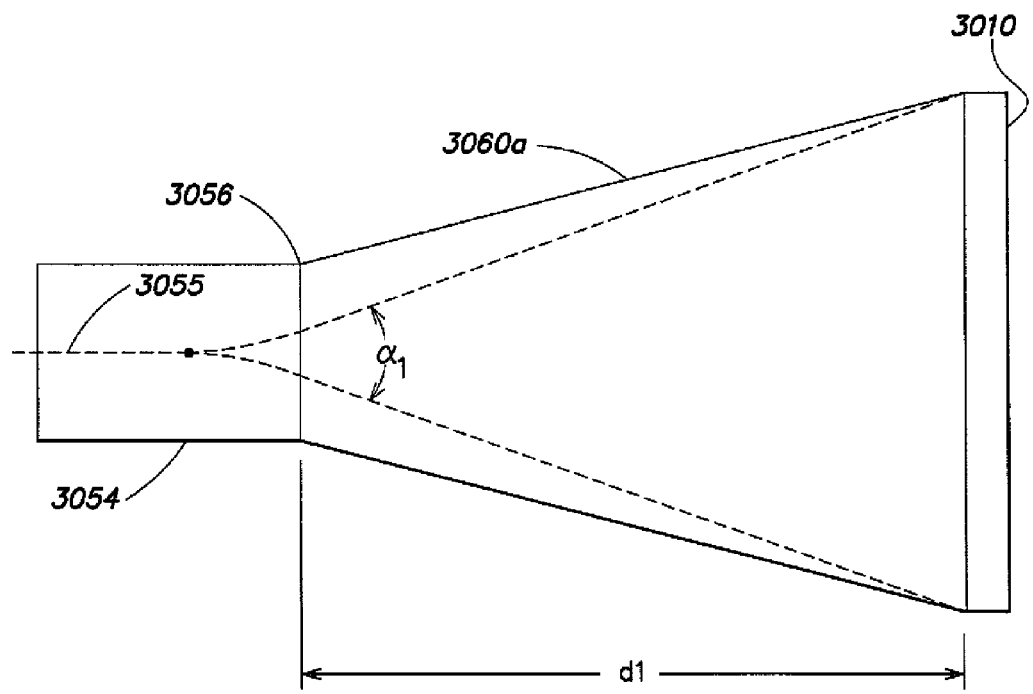
FIGS. 30A and 30B illustrate reducing the size of the vacuum tube in an electron beam generator using various aspects of the present invention.
Figure 30B:
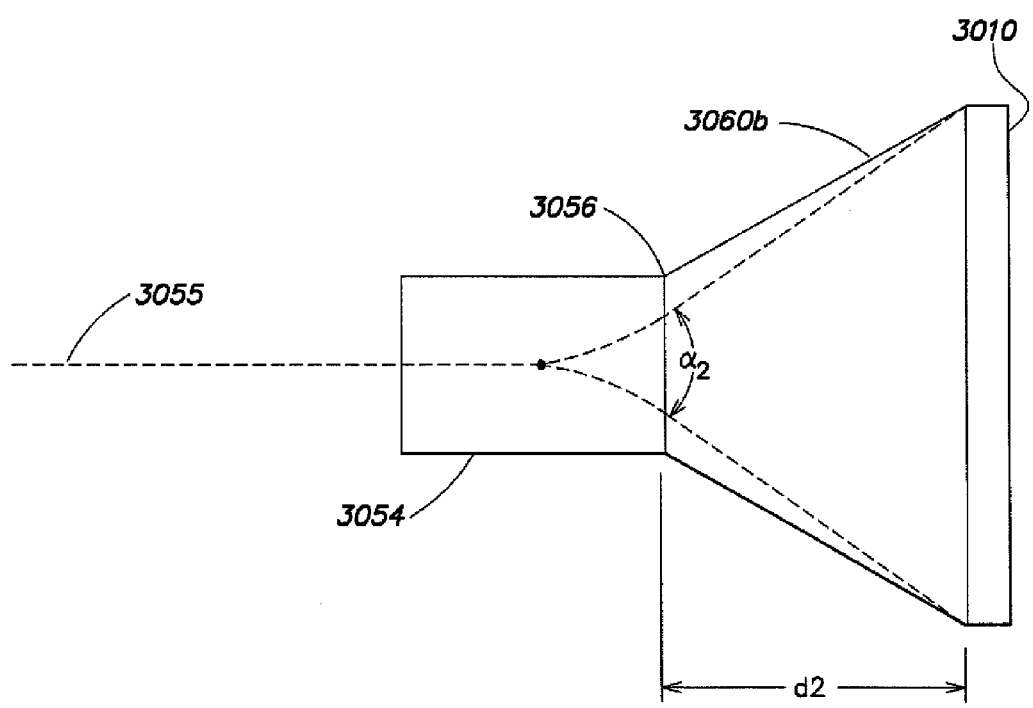

FIGS. 30A and 30B illustrate the relationship between deflection angle and the distance between the e-beam generator and the target. In FIG. 30A, a steering mechanism 3054 bends an e-beam 3055 at a deflection angle $\alpha_1$. It should be appreciated that once the e-beam is no longer under the forces of the steering coils, the trajectory of the e-beam becomes substantially linear. The point at which an e-beam is no longer under the effects of the steering coils (e.g., when the e-beam trajectory is essentially linear and has effectively no curvature) is referred to as the exit point of the e-beam, and is situated at the exit port 3056 of the steering mechanism.

In FIG. 30A, a vacuum tube 3060a having a length $d_1$ is needed to accommodate the e-beam generated with deflection angle $\alpha_1$ such that the entire sweep of target 3010 may be scanned. FIGS. 30A and 30B may be a top view of an e-beam generator target combination. For example, target 3010 may be the cross-bar of a substantially U-shaped or rectangular shaped target (e.g., portion 2012b illustrated in FIG. 2). In FIG. 30B, the deflection angle is increased to $\alpha_2$. As a result, vacuum tube 3060b need only have a length $d_2$ to accommodate the e-beam. Accordingly, as the deflection angle is increased, the distance between the exit port 3056 and target may be reduced and the vacuum tube may be decreased in size. Thus, if the constraints on the deflection angle are relaxed, the deflection angle may be held constant while decreasing the distance between the exit point and the target.

Figure 31A:
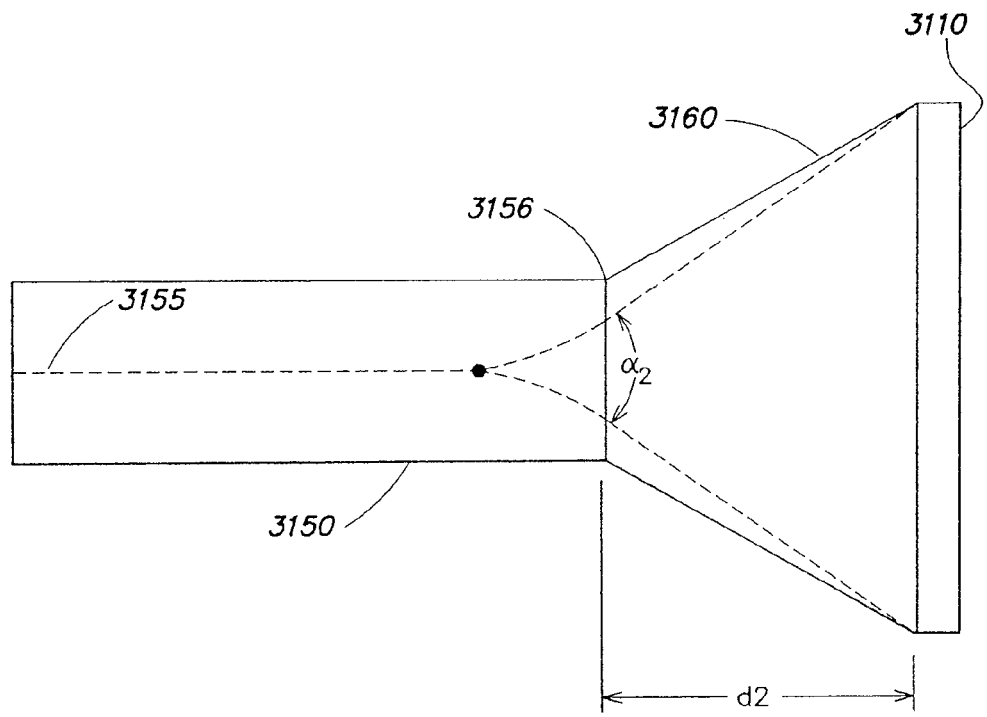
FIGS. 31A and 31B illustrate reducing the size of the vacuum tube in an electron beam generator using various aspects of the present invention related to dual electron beam generators.
Figure 31B:
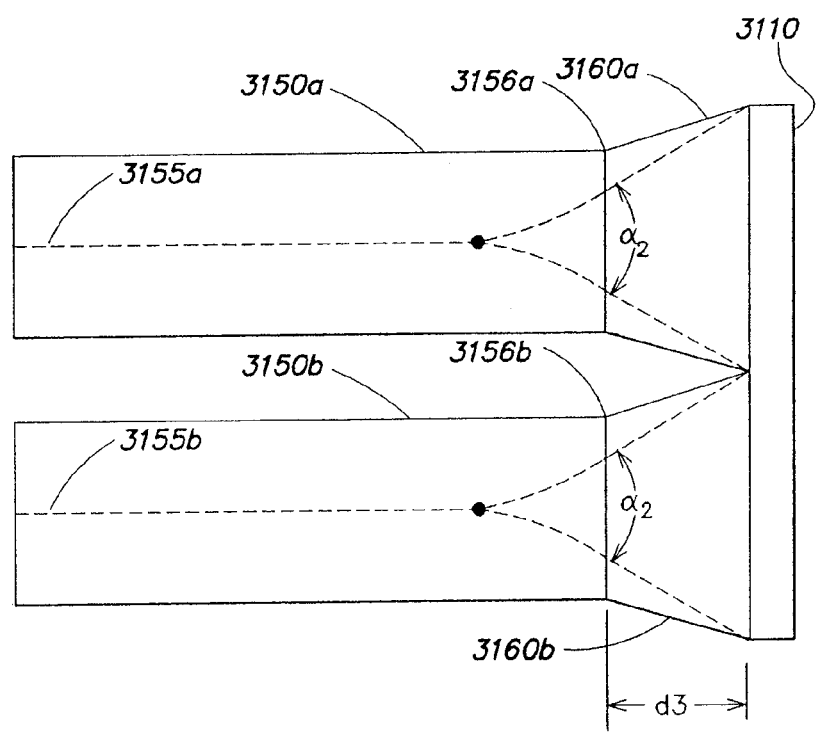

For example, FIG. 31A illustrates a configuration wherein a single e-beam generator 3150 is responsible for scanning target 3110. At a deflection angle $\alpha_2$, the vacuum tube 3160 needs a length of $d_2$ to accommodate the e-beam as described in FIG. 30B. In FIG. 31B, two electron generators 3150a and 3150b are arranged to scan essentially half of target 3110. As a result, the deflection angle required to cover the half of the target 3110 that each e-beam generator is respectively responsible for scanning may be reduced. However, rather than decreasing the deflection angle, the e-beam generators may be moved closer to the target. Accordingly, at deflection angle $\alpha_2$, vacuum tubes 3160a and 3160b may accommodate the respective e-beams with a distance $d_3$ that is substantially less than distance $d_2$. Thus, the x-ray scanning system may be made more compact.

It should be appreciated that the two vacuum tubes 3160a and 3160b together have an area smaller than the area of single vacuum tube 3160. Accordingly, the two vacuum tubes not only facilitate a reduced footprint x-ray system, but may facilitate the manufacture of a less expensive x-ray system. While the advantage gained by using multiple e-beams is exploited to reduce the length of the vacuum tube, it may also be used to decrease the deflection angle that the steering coils need achieve. In particular, the length of the vacuum tube may remain the same as in single e-beam generator configurations while reducing the deflection angle. In addition, some combination of vacuum tube length reduction and deflection angle reduction may be used together. That is, the benefits accorded by multiple e-beam generators may be shared between reducing deflection angle and/or reducing the distance between the exit point and the target, in any amount or combination, as the aspects of the invention are not limited in this respect.

Figure 32A:
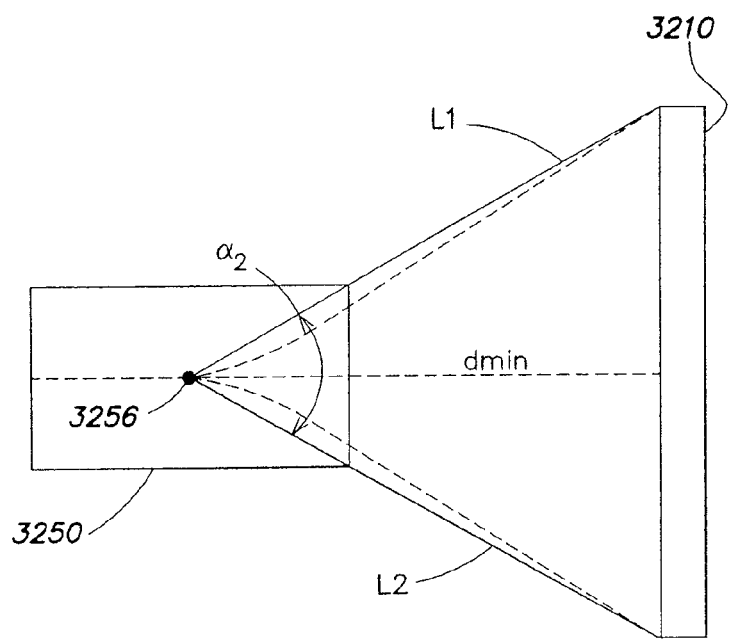
FIGS. 32A-32C illustrate various concepts for reducing the sweep angle and minimum distance between the exit port of an electron beam generator and the target, in accordance with various aspects of the present invention.

Applicant has appreciated that configurations made possible by multiple e-beam generators facilitate further reduction in deflection angle and/or vacuum tube size. FIG. 32A illustrates an e-beam generator 3250 arranged to scan target 3210. For example, target 3210 may be the portion of the target 3110 that e-beam generator 3150a is responsible for scanning or another portion of a target (e.g., target 3210 may be portion 2012a of target 2010 illustrated in FIG. 2). E-beam generator 3250 is positioned generally symmetric to target 3110. In particular, the length $L_1$ of the line connecting center point 3256 (i.e., the point at which the e-beam begins being bent by the steering mechanism) to one extreme of the target 3210 and the length $L_2$ of the line connecting center point 3256 and the other extreme of the target 3210 are substantially equal. The two lines of length $L_1$ and $L_2$ respectively define the sweep of the electron beam and is related to the required deflection angle imposed on the steering mechanism. In addition, the minimum distance $d_{min}$ between center point 3256 and the target is along the line from the center point to the center of the target.

Figures 32B, 32C:
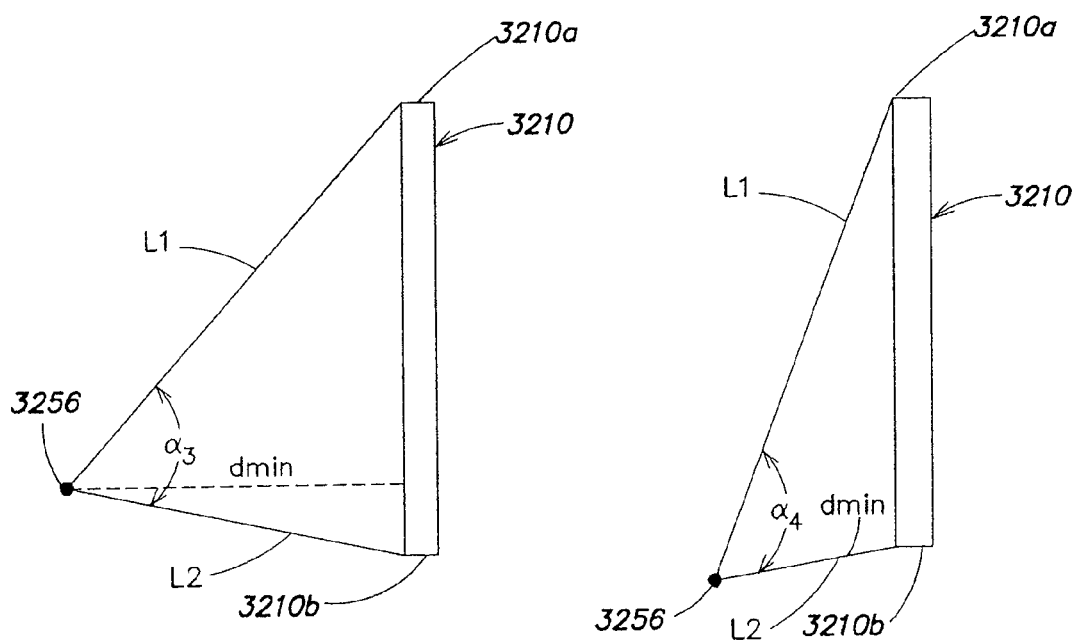

Applicant has appreciated that by re-configuring the location of the e-beam generator, the sweep of the e-beam may be reduced, thus reducing the deflection angle required of the steering mechanism. In addition, the minimum distance between the e-beam generator and the target may be decreased, thus facilitating more compact vacuum tube construction. In particular, asymmetrical placement of e-beam generators allows the reduction of the sweep required by the steering mechanism and reduces the length of the vacuum tube needed to accommodate the e-beam. FIGS. 32B and 32C illustrate e-beam generator configurations, in accordance with the various embodiments of the present invention.

In FIG. 32B, the e-beam generator has been positioned such that the center point 3256 is located closer to extreme 3210b of target 3210 then to extreme 3210a of target 3210. As a result, the sweep of the e-beam as defined by $\alpha_3$ is smaller than the sweep of the e-beam in FIG. 31A (as defined by $\alpha_2$). As a result, the configuration imposes reduced deflection angle requirements on the steering mechanism. In addition, the minimum distance $d_{min}$ in FIG. 32B has been reduced from the minimum distance in the configuration illustrated in FIG. 32A. Accordingly, the reduced sweep angle and minimum distance facilitate smaller and more compact construction for the x-ray scanning system, and more particularly, smaller more compact vacuum tube construction.

In FIG. 32C, the e-beam is moved even further in the direction of extreme 3210b. As expected, both the sweep angle $\alpha_4$ and the minimum distance are smaller than the configuration in FIG. 32B. It should be appreciated that as the e-beam generator is positioned asymmetrically with the target, the e-beam will impinge on the detector array at increasingly oblique angles, effecting the eccentricity of the focal spot. To compensate for changes in the focal spot of the e-beam, the steering mechanism may include focusing means to reshape the electron beam to compensate for the oblique angles at which the e-beam impinges on the target. As discussed above, reductions in required deflection angles may be exploited as actual deflection angle requirements, as reductions in distance between the e-beam generator and the target, or a combination of both. Various configurations that utilize concepts related to asymmetric positioning of the e-beam generator are shown in FIGS. 14 and 25-27, which are discussed in further detail below.

As discussed above, multiple e-beam generators may be arranged to scan substantially half of a target. In another embodiment, each electron gun scans more than half of the target. For example, it may be desirable for the path of the electrons guns to overlap in a region that includes the seam between the portions of the target that the electrons are respectively responsible for scanning. To achieve the overlap, the first electron gun may provide an e-beam along a path to scan portion 2010a and a relatively small region 2010c extending into portion 2010b. Similarly, the second electron gun may provide an e-beam along a path to scan portion 2010b and a relatively small region 2010d extending into portion 2010a. Information obtained from the resultant overlap region in the two scan paths allows for interpolation so that attenuation values are relatively smooth across the transition point in the paths of the respective electrons guns. However, an overlap region need not be employed, as the aspects of the invention are not limited in this respect.

The application of multiple electron guns allow each beam to be deflected less to reach desired locations along the target. As a result of the reduced deflection angle, the electron guns may be positioned closer to the target, decreasing the length and size, generally, of the vacuum tube(s) and the associated apparatus. In one embodiment, the field-free path of the e-beam from the electron gun to the anode may be reduced approximately by a factor of two, resulting in a less expensive, more compact X-ray scanning system. For example, the smaller vacuum tubes and reduced shielding requirements facilitate less expensive construction having a reduced footprint.

In one embodiment, a pair of electron guns is housed in a single vacuum tube and is positioned and oriented to scan respective portions of the target via the same vacuum tube. In an alternative embodiment, each of a pair of electron guns are housed in respective and independent vacuum tubes, disposed to scan respective portions of the target. Other electron gun/vacuum tube arrangements may be used, as the aspects of the invention are not limited in this respect. FIGS. 8-16 illustrate various arrangements of an X-ray system employing two e-beam generators (guns), in accordance with different embodiments of the present invention. In the embodiments illustrated in FIGS. 8-16, the target is substantially horseshoe shaped and the detector array is substantially u-shaped. However, it should be appreciated that both the target and detector array may be of substantially the same shape, or of different shapes not illustrated herein, as the aspects of the invention are not limited in this respect.

Figure 14A:
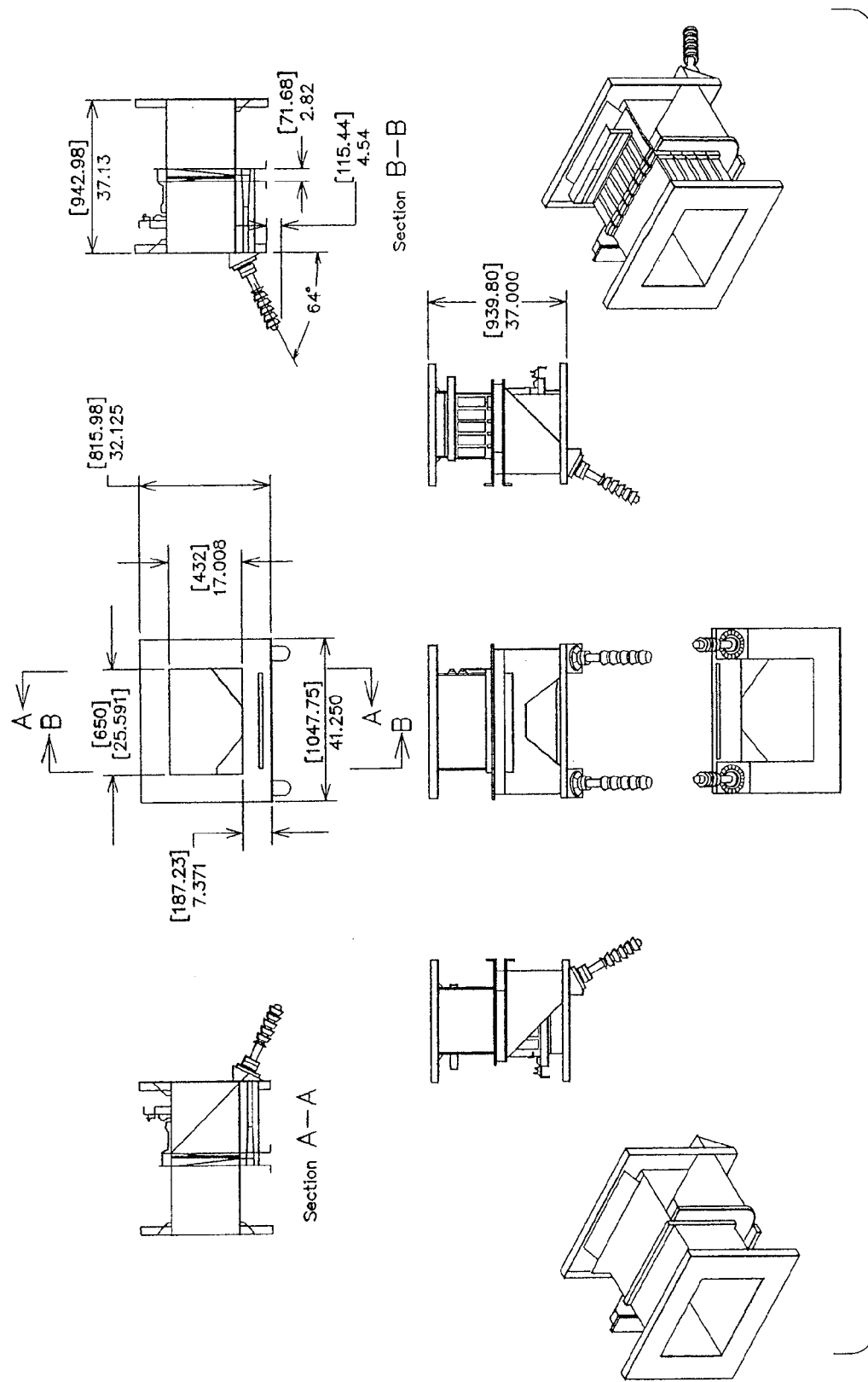

FIG. 14A illustrates a configuration that utilizes various aspects of asymmetric positioning of e-beam generators. Different views of portions of an x-ray detection system illustrated in FIG. 14A are illustrated in greater detail in FIGS. 14B-14F. In particular, FIG. 14B illustrates a side view of one e-beam generator. E-beam generator 1450a is arranged to provide an e-beam to impinge on a portion of a target 1410. E-beam generator 1450a is positioned closer to target extreme 1410b then target extreme 1410a to reduce the sweep angle of the e-beam generator. As shown, the boundary of vacuum tube 1460a from the e-beam generator to target extreme 1410b forms substantially a right angle with the target. However, other configurations are possible, as the aspects of the invention are not limited in this respect.

Figure 14D:
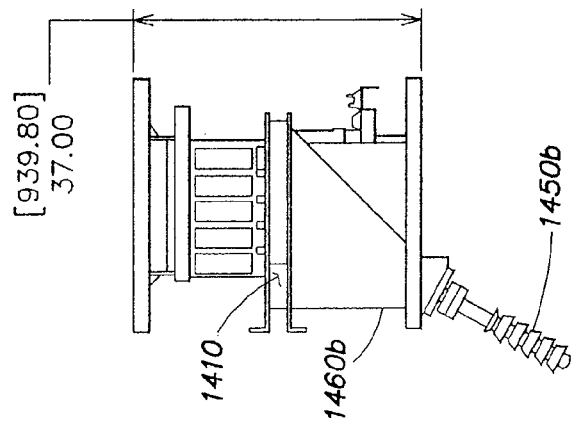
Figure 14C:
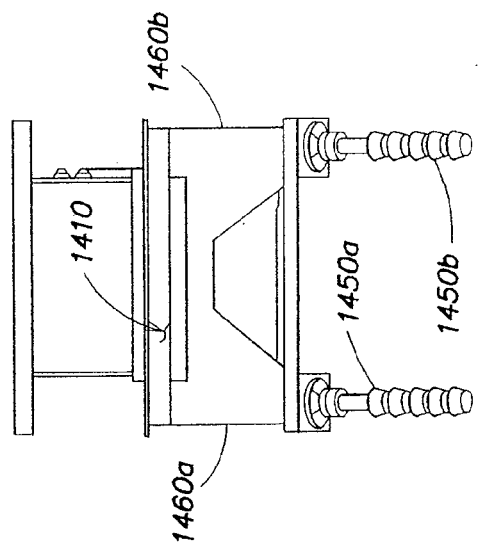
Figure 14B:
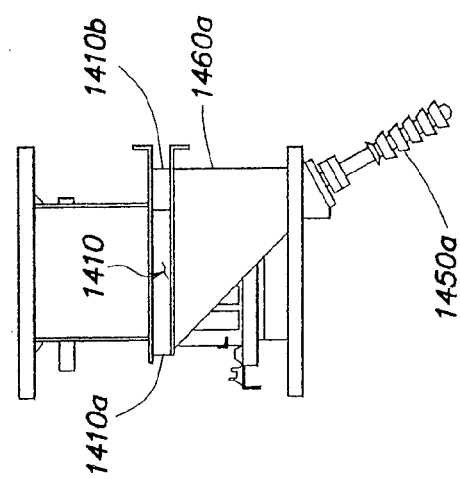
Figure 14E:
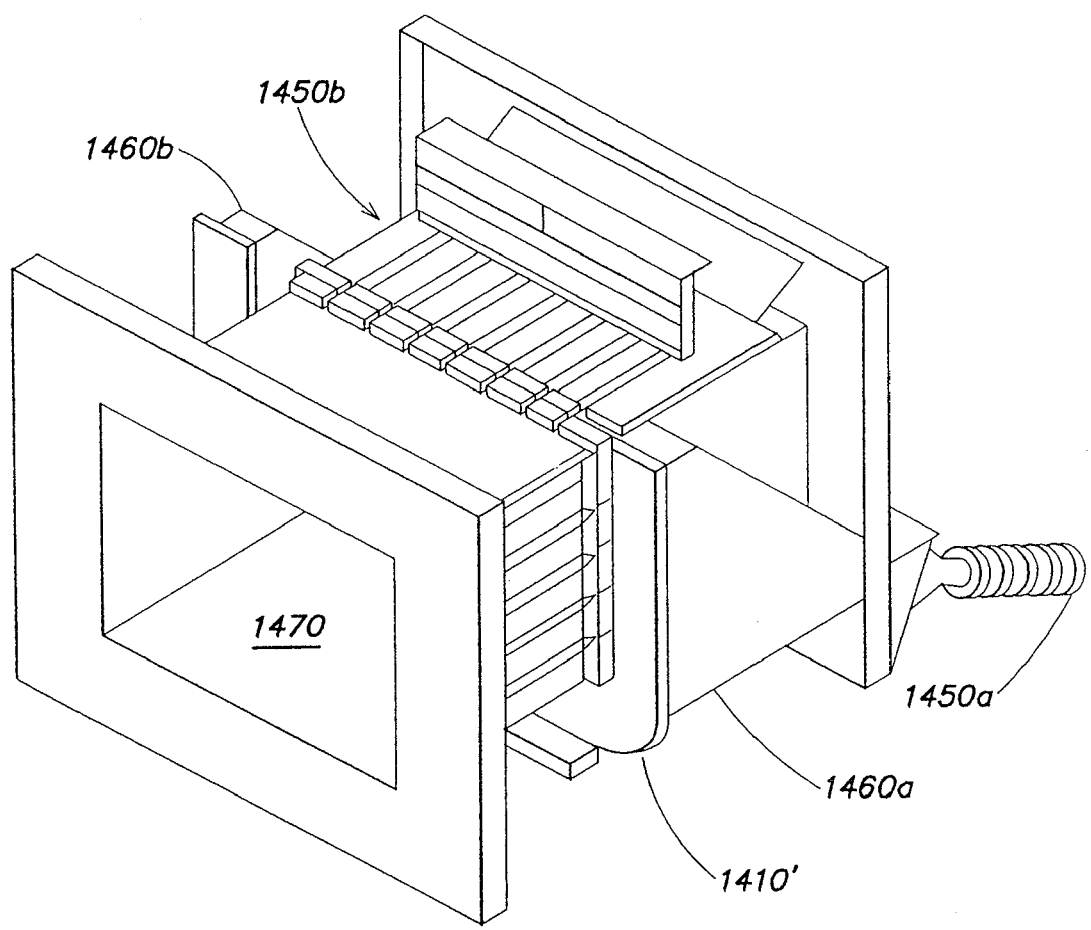
Figure 16:
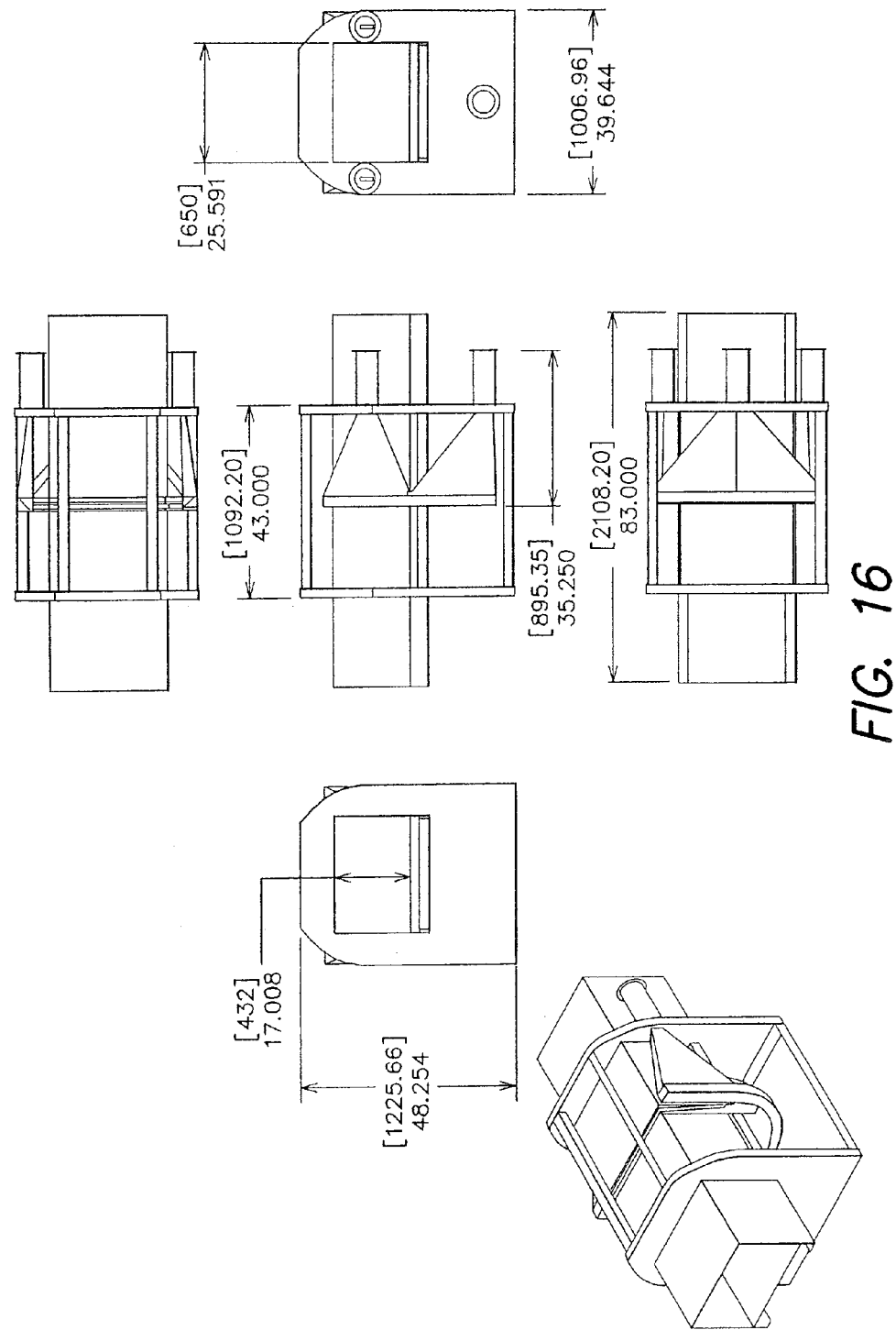
Figure 17:
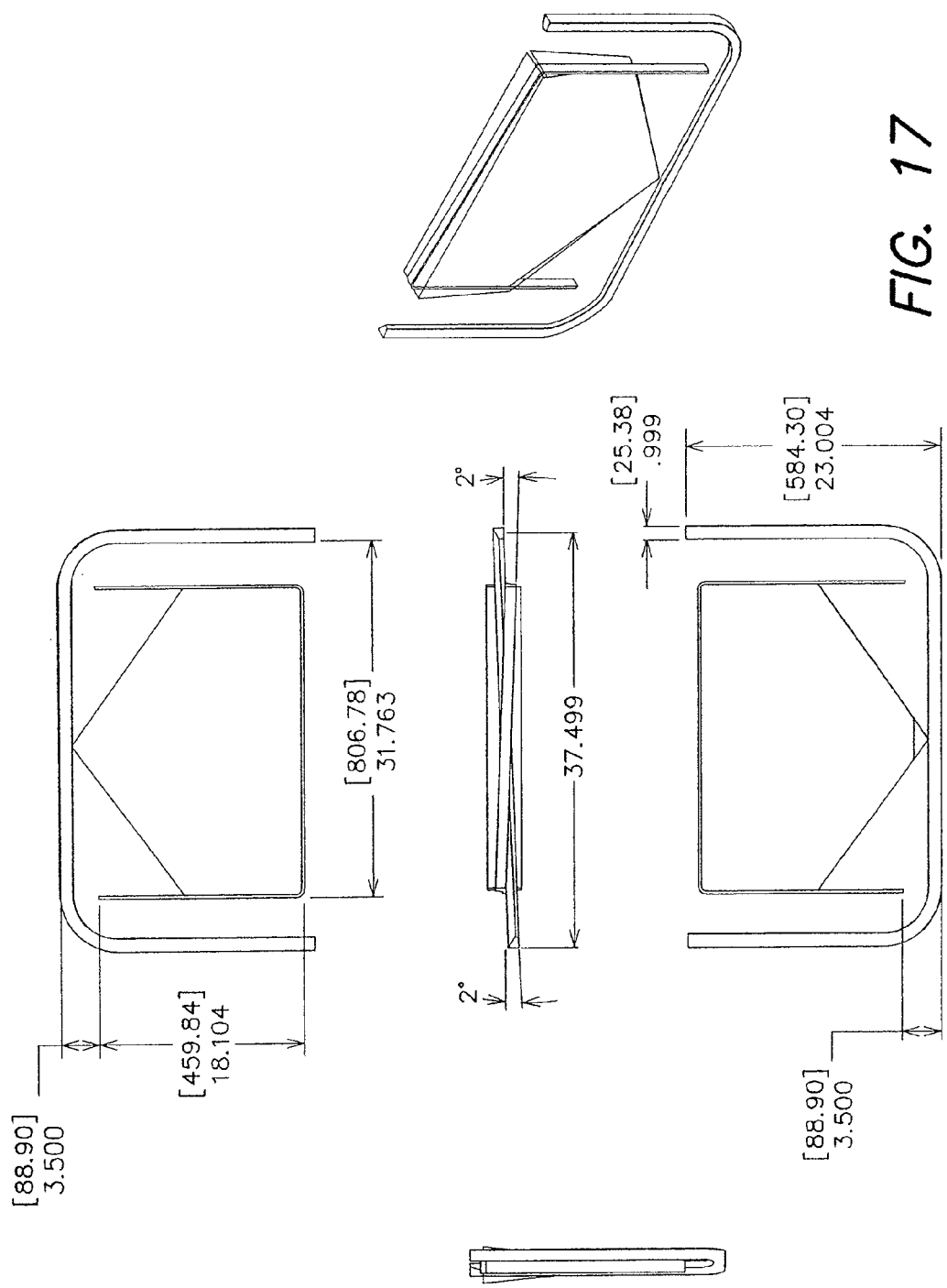
FIGS. 17-23 illustrate various configurations utilizing rotation between the target and the detector array, in accordance with various embodiments of the present invention.
Figure 18:
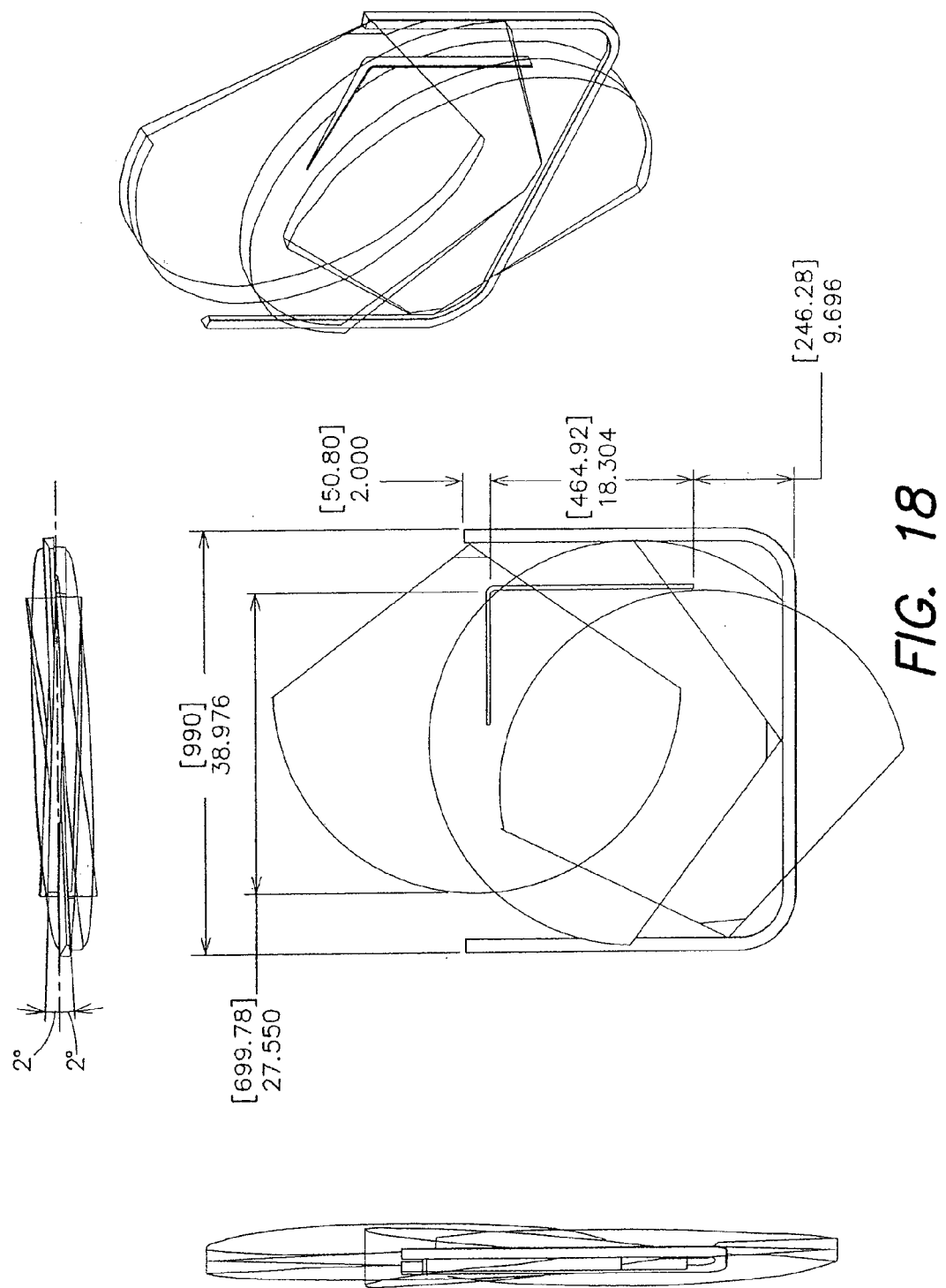
Figure 19:
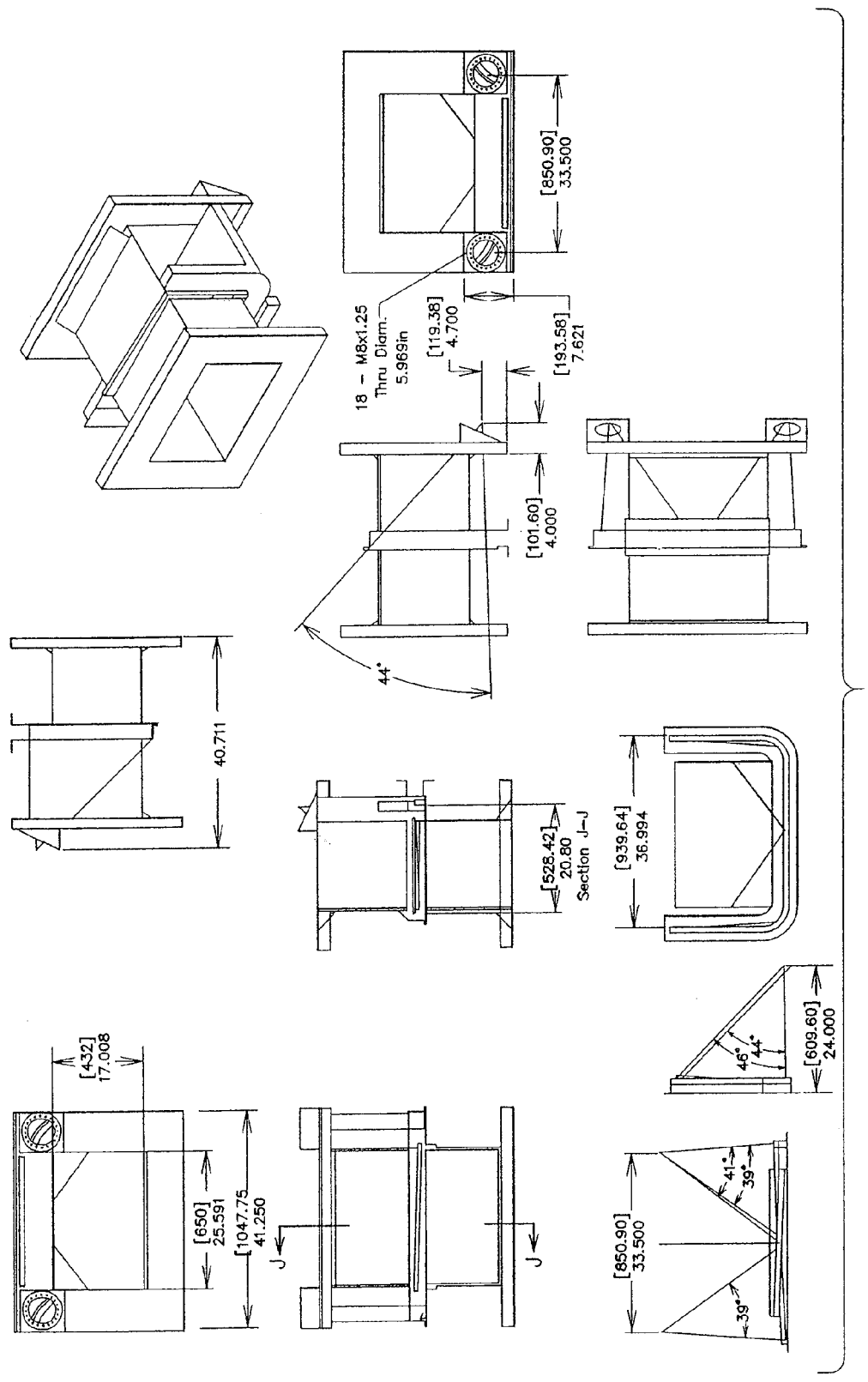
Figure 20:
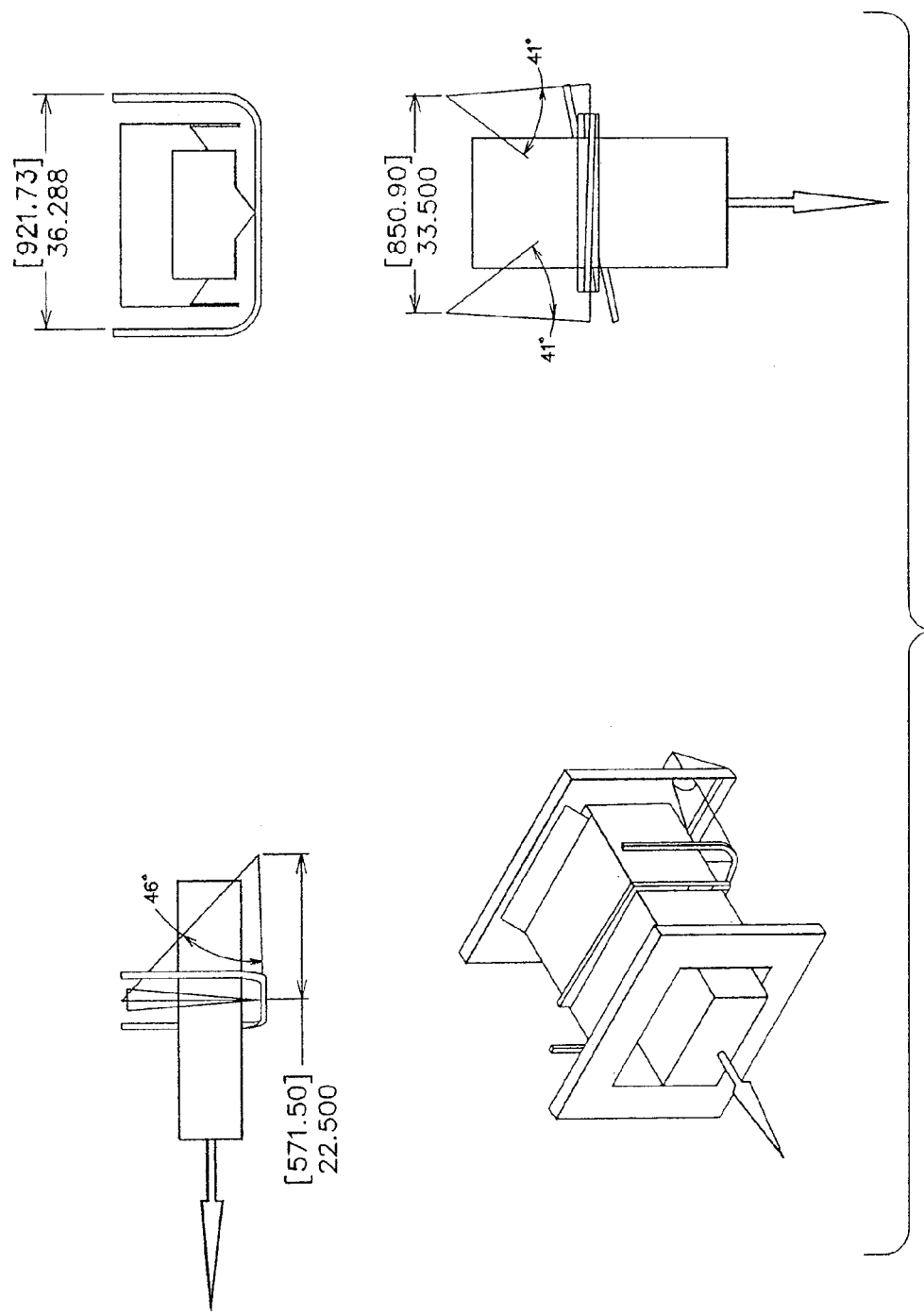
Figure 21:
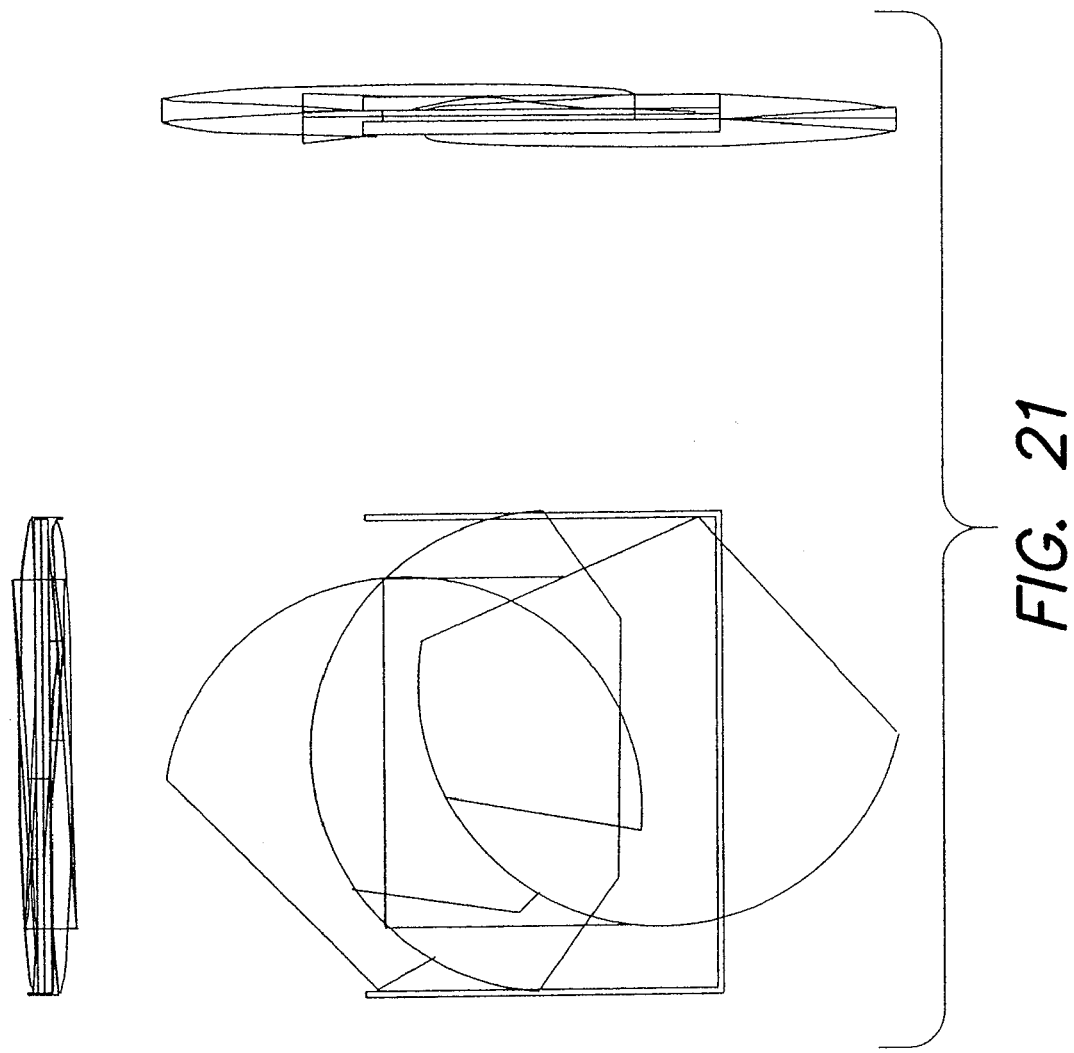
Figure 22:
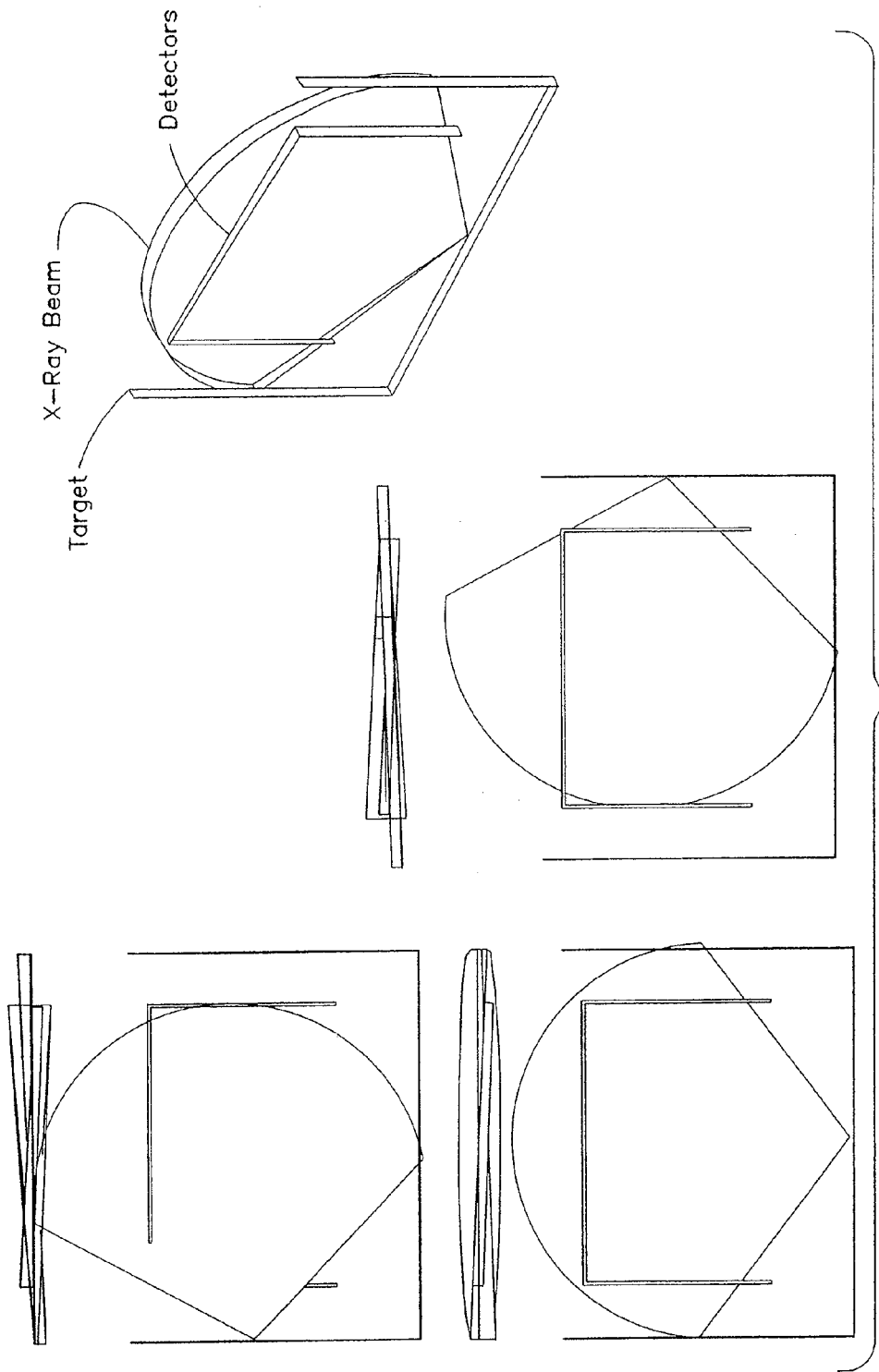

FIG. 14D illustrates another e-beam generator 1450b arranged to provide an e-beam to impinge on another portion of target 1410. E-beam generator may be arranged to mirror e-beam generator 1450a as shown in the top view of a portion of an x-ray scanning device in FIG. 14C, which shows the arrangement of both e-beam generators. FIG. 14E illustrates how the two e-beam generators 1450a and 1450b (behind tunnel 1470) are positioned with respect to a tunnel 1470 through which objects of interest are conveyed. As shown, each of e-beam generators 1450a and 1450b are positioned to provide e-beam energy to impinge on approximately half of substantially U-shaped target 1410' to emit x-rays in an inspection region internal to the tunnel 1470.

As discussed above, targets of any arbitrary geometry may be used. In FIG. 2, the various segments that form the target are provided continuously. However, in some embodiments, each of the segments are provided at an offset with respect to one another. For example, the linear segment 2012a may be provided at a first depth $z_0$, the circular segment 2014a may be provided at a second depth $z_1$, the linear segment 2012b may be provided at a third depth $z_2$, the circular segment 2014b may be provided at a fourth depth $z_3$, and the linear segment 2012c may be provided at a fifth depth $z_4$, wherein the depths $z_i$ increase in the direction of an item being conveyed through the inspection system. Any one or combination of segments may be offset from the other segments. Likewise, any one or combination of the segments of the detector array may be staggered in the direction of conveyance, or otherwise staggered or offset, as the aspects of the invention are limited in this respect.

Figure 3:
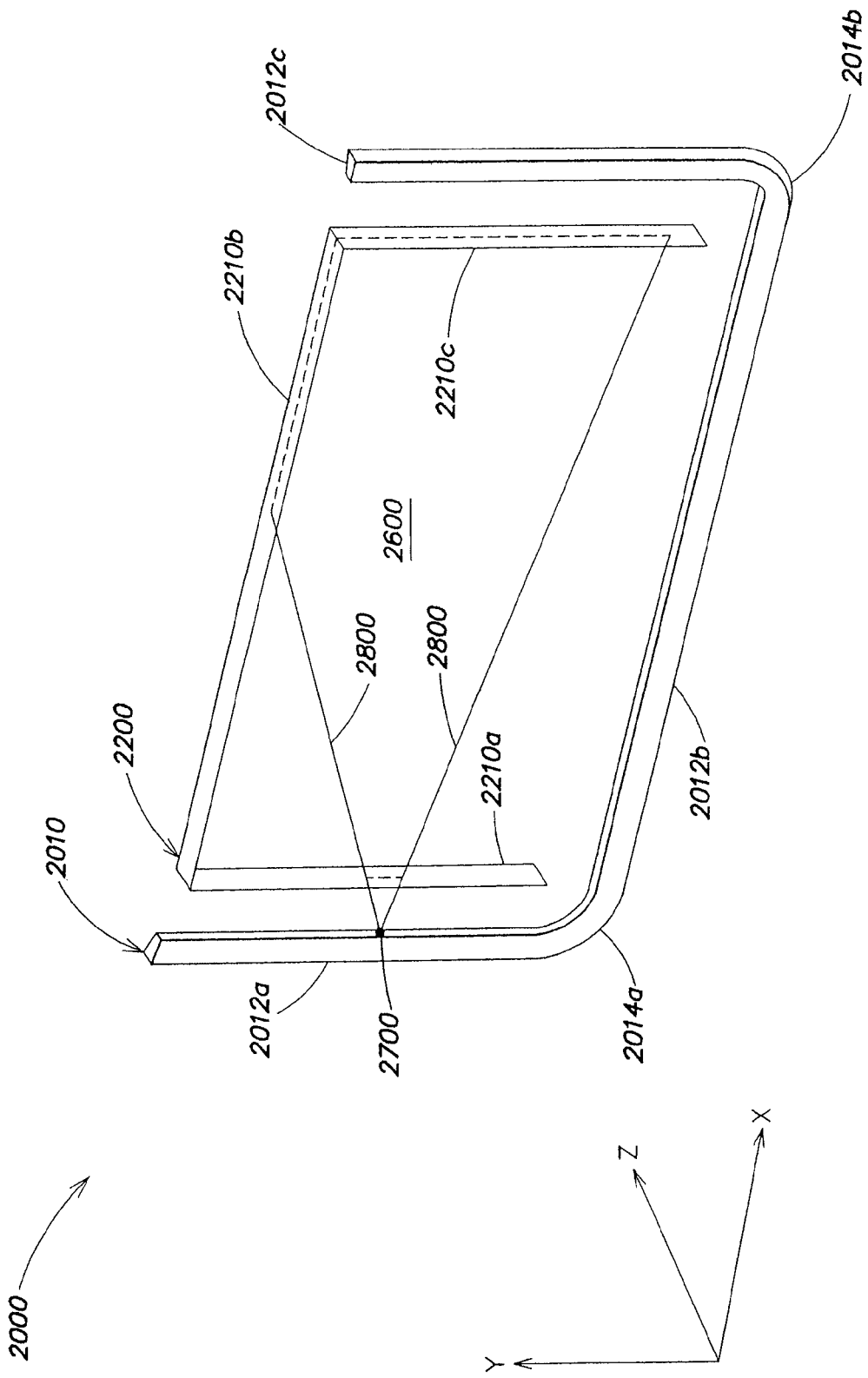
FIG. 3 illustrates near-side detector irradiation occurring in the arbitrary geometry target and detector array of FIG. 2.

Referencing FIG. 3 (illustrating substantially the same system as FIG. 2), to scan an object positioned in examination region 2600, an e-beam is directed to impinge on target 2010, which responds by emitting X-rays in the $4\pi$ directions. The emitted X-rays are then typically shaped by a desired configuration of one or more collimators to form a fan beam, a pencil beam or other shaped beam that enters the inspection region to penetrate an object being scanned, and to subsequently impinge on the diametrically opposed detectors after exiting the object, thus recording information about the interaction of the X-ray beam with the object.

In FIG. 3, collimators (not shown) are arranged such that at each point along target emitted X-rays are absorbed except for a fan of X-rays substantially in a plane that is permitted to pass into the inspection region. The fan beam enters the inspection region 2600 and penetrates the object being scanned. The detectors in detector array 2200 respond to X-rays generated from a diametric portion of the target. For example, the detectors along arms 2210b and 2210c of the detector array 2200 detect X-rays in the fan beam generated along arm 2012a of the target, as illustrated by exemplary fan beam 2800 emitted by X-ray source location 2700. As a result, when the detector array is substantially aligned in the same plane as the target, fan beam 2800 passes through the near side of the detector array (e.g., arm 2210a of the detector array) before entering the inspection region and ultimately impinging on the portion of the detector array intended to record attenuation information (i.e., the far side detectors).

The unintentional irradiation of portions of a detector array (e.g., the detector highlighted with a dotted line along arm 2210a) may be undesirable for a number of reasons. In particular, the unintentional irradiation of near side detectors (i.e., detectors not substantially diametric to the fan beam, such as the detectors positioned on the near side of the inspection region with respect to the X-ray source) causes the near side detectors to respond. However, the X-rays impinging on the near side detectors do not carry information about the object being scanned because the X-rays have not penetrated the inspection region, and thus the object, before impinging on the near-side detectors. Accordingly, the near side detectors will be generating spurious detection signals.

In addition, the near side detectors will interact with the X-rays causing some changes to the X-rays before they enter the inspection region. As such, the X-rays impinging on the intended detectors (e.g., the far side or diametric detectors) will have been modified by subject matter other than the object being scanned. Stated differently, some of the changes in the X-rays do not carry information because they correspond to the near side detectors and not the object being scanned, and more importantly, the near-side detectors block a significant and substantial portion of the x-rays from entering the inspection region as the detectors are designed to intercept a majority of x-rays impinging on their surface.

Figure 4:
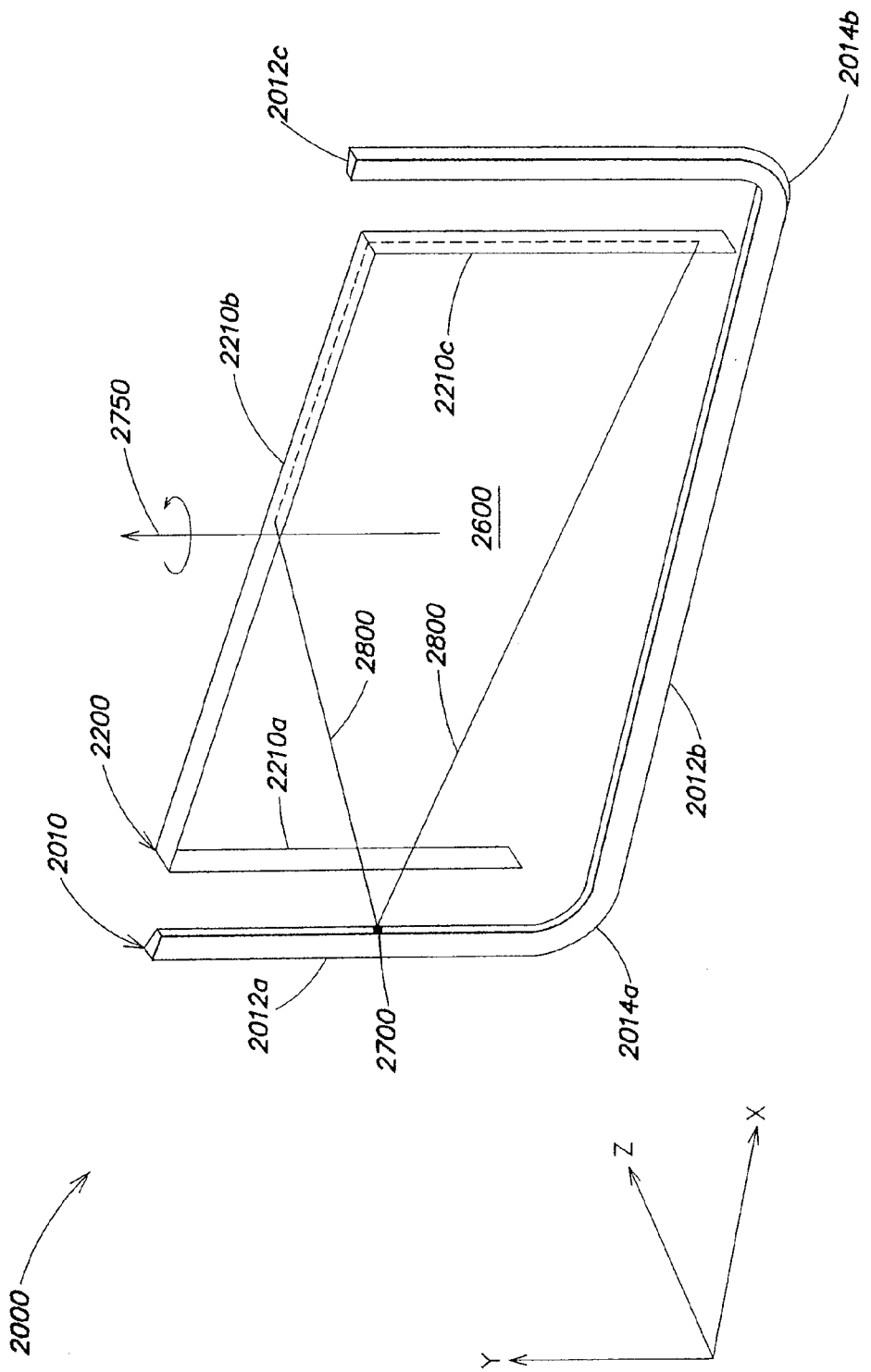
FIG. 4 illustrates an arbitrary geometry target and detector array configuration in which the target and detector array are rotated with respect to one another, in accordance with one embodiment of the present invention.

To prevent near-side detector irradiation, the plane of the detector array may be rotated with respect to the plane of the target. For example, in FIG. 4, detector array 2200 may be rotated about axis 2750. Accordingly, a fan beam emitted from locations along the target will avoid the near-side detectors, enter the inspection region and impinge on the far side detectors. For example, a fan beam generated from X-ray source point 2700 will pass by (and not through) detectors along portion 2210a of the array and impinge on detectors along portions 2210b and 2210c as intended. It should be appreciated that either the detector array or target may be rotated as long as the respective planes are positioned non-parallel to one another. In addition, other modifications may be used to effect an offset between the detector array and target planes to prevent near-side detector exposure.

It should be appreciated that the target generally surrounds, at least in part, a generally planar region. X-rays emitted from the target are generally collimated to permit only the x-rays substantially in this plane to enter an inspection region. Similarly, the detector array also surrounds, at least in part, a generally planar surface, for example, the plane comprising the vector normals of the detector surfaces of the detector array. Thus the planes formed by the target and detector arrays are the cross-sections of the inspection area through which objects to be inspected are moved and/or conveyed. As discussed above, by rotating these planes with respect to one another such that they are non-parallel and non-coplanar, near-side detector irradiation may be prevented. FIGS. 17-22 illustrate various configurations of providing non-coplanar target and detector arrays to avoid near-side detector penetration, in accordance with other embodiments of the present invention.

Figure 24A:
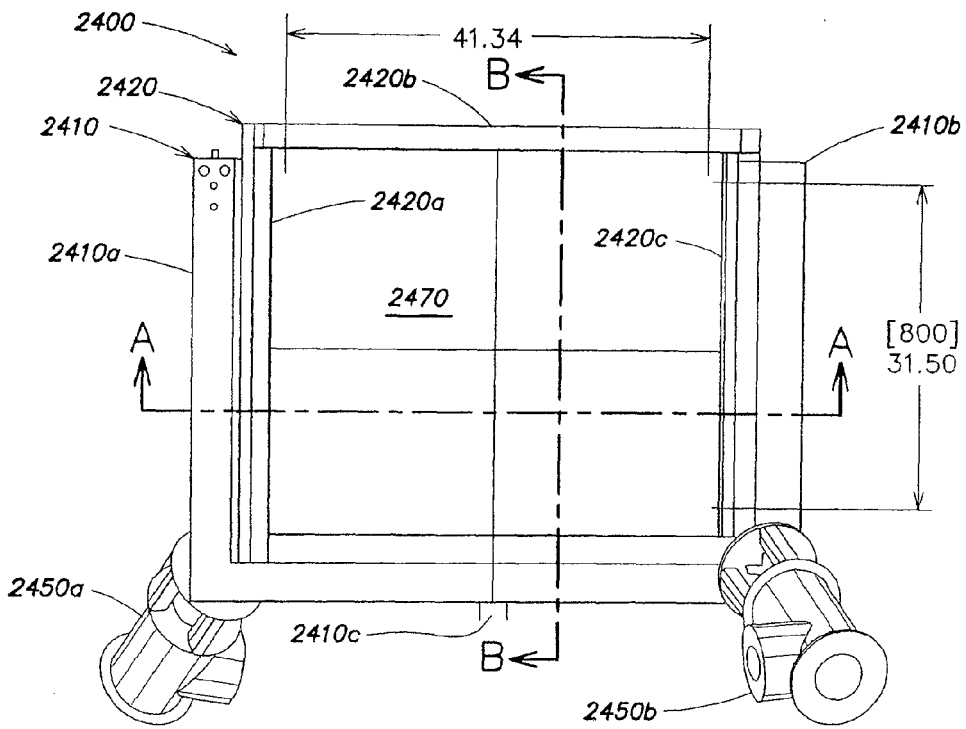
FIGS. 24-27 illustrate portions of an x-ray scanning system using dual and opposing electron beam generators, in accordance with various embodiments of the present invention.
Figure 24B:
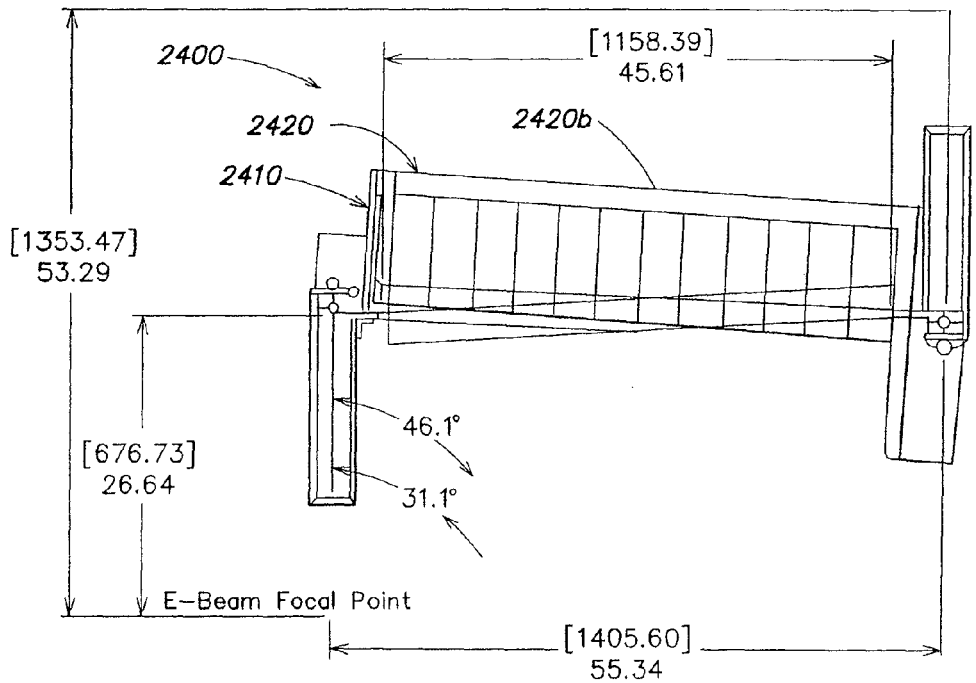
Figure 24C:
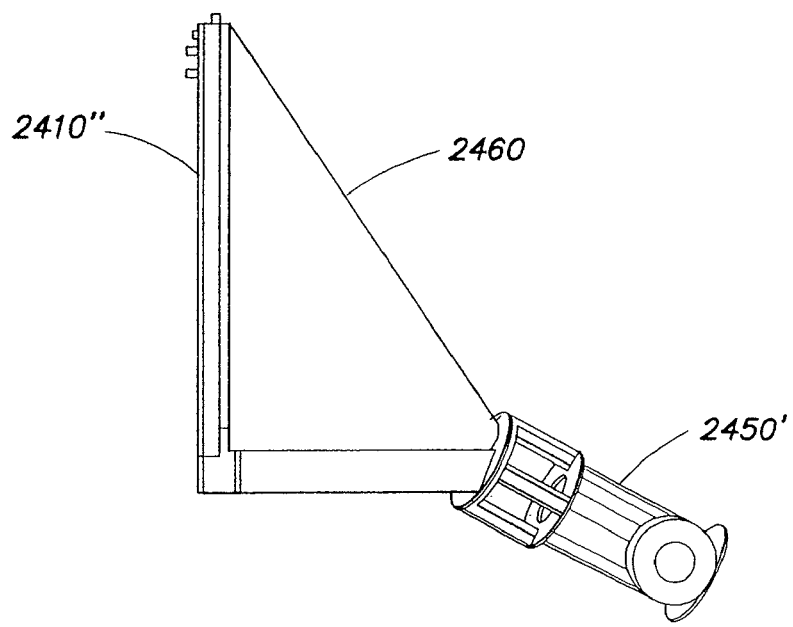
Figure 24D:
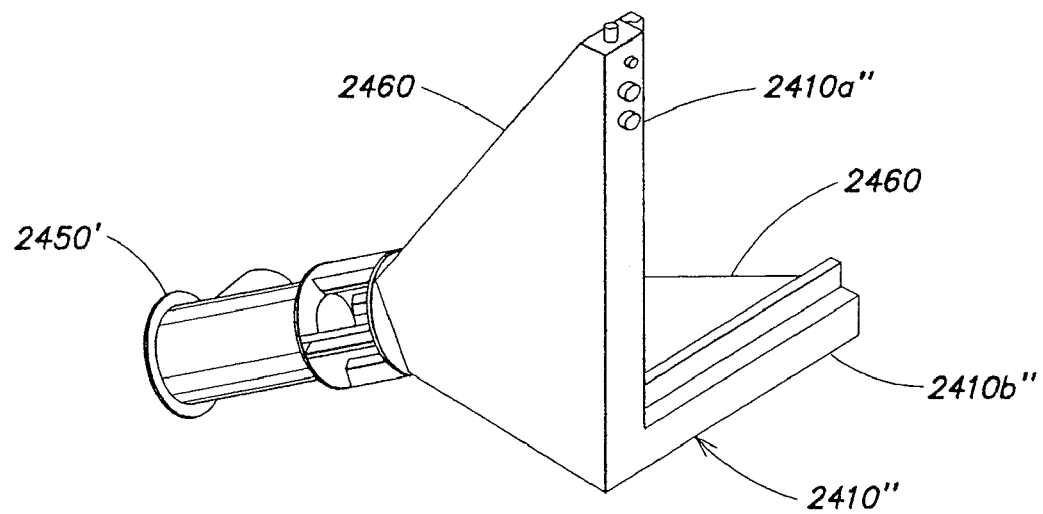

FIGS. 24A and 24B illustrate an X-ray scanning system employing two e-beam generators/guns arranged on opposite sides of the detector array, in accordance with another embodiment of the present invention. FIG. 24A illustrates the X-ray scanning system from a front view and FIG. 24B illustrates the X-ray scanning system from a top view. X-ray scanning system 2400 includes a generally rectangular shape detector array 2420 and generally rectangular shaped target 2410. The target and detector array have respective portion arranged diametrically such that X-rays emitted from the target impinge on the opposing portions of the detector array. The target and detector array form an inspection region 2470 though which objects to be inspected pass. That is, objects to be inspected pass through the planes formed by both the target and the detector array to be exposed to the X-rays emitted by the target.

A first e-beam generator 2450a is positioned on a first side of the detector array and generates an e-beam that is directed to impinge on L-shaped portion 2410a of target 2410. A second e-beam generator 2450b is positioned on a second side of the detector array and generates an e-beam that is directed to impinge on portion 2410b of target 2410. It should be appreciated that the e-beam generators or electron guns are arranged on opposite sides of the inspection region 2470. The plane formed by the target or the plane formed by the detector array may be viewed as dividing the X-ray scanning device into the first side and the second side. Before an object enters the inspection region it is on the first side and, similarly, after the object has passed through the inspection regions it is on the second side.

In FIG. 24, the first e-beam generator is generally facing towards object passing through the inspection region. That is, the e-beam generated by e-beam generator 2450a, absent deflection forces, is emitted in a direction that generally opposes the direction of motion of the object. Similarly, e-beam generator 2450b is generally facing with the object passing through the inspection region (i.e., the e-beam generated by e-beam generator 2450a, absent deflection forces, is emitted in a direction that generally agrees with the direction of motion of the object. E-beam generators 2450a and 2450b may be tilted or angled such that the e-beam, absent deflection forces, is generated at any desired angle with respect to the direction of motion of the objects passing through the inspection region, as the aspects of the invention are not limited in this respect. Likewise, e-beam generators 2450a and 2450b may be positioned anywhere on the respective sides, or on the same side as illustrated in FIGS. 8-23, as the aspects of the invention are not limited for use with any particular configuration of e-beam generator(s).

The operation of the e-beam generators 2450a and 2450b may be timed such that they scan respective portions of the target in succession. For example, e-beam generator 2450a may be energized such that portion 2410a of target 2410 is impinged along a scanning path from the top of L-shaped portion 2410a to the bottom where portion 2410a meets portion 2410b. During this first interval, e-beam generator 2450b may be de-energized such that no e-beam energy impinges on portion 2410b. When e-beam generator 2450a reaches the end of its respective portion of the target, generator 2450*a* may be turned off and generator 2450*b* may be energized to scan portion 2410*b*. Generator 2410*b* may be arranged such that the e-beam emitted from the generator impinges on the portion 2410*b* at the bottom side where the two portions meet at the beginning of the interval and scans up the target to the top of the L-shaped portion.

In this way, the targets are independently scanned during subsequent intervals. It should be appreciated that there may be an overlap region 2410*c* where both e-beam generators direct e-beams to impinge on the overlap region of the target, as discussed above in connection with FIGS. 2-4. Overlap region 2410*c* is shown in FIG. 24 schematically and, when present, may be of any size or located anywhere on the target. It should be appreciated that the target need not include an overlap region, as the aspects of the invention are not limited in this respect. The e-beam generators may be controlled to scan their respective targets at a constant velocity or at a variable scanning rate, as discussed in further detail below.

Figure 25A:
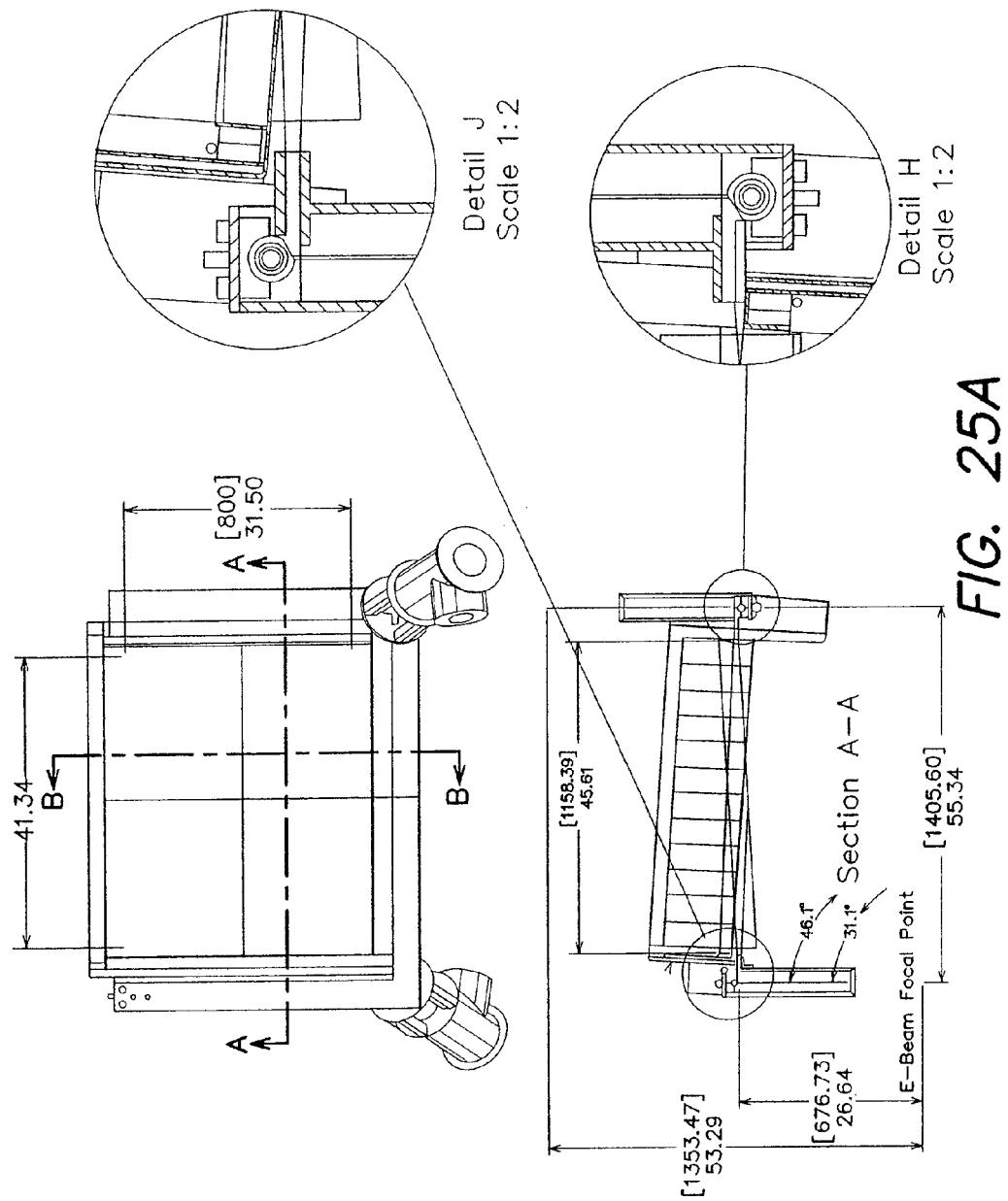
Figure 25B:
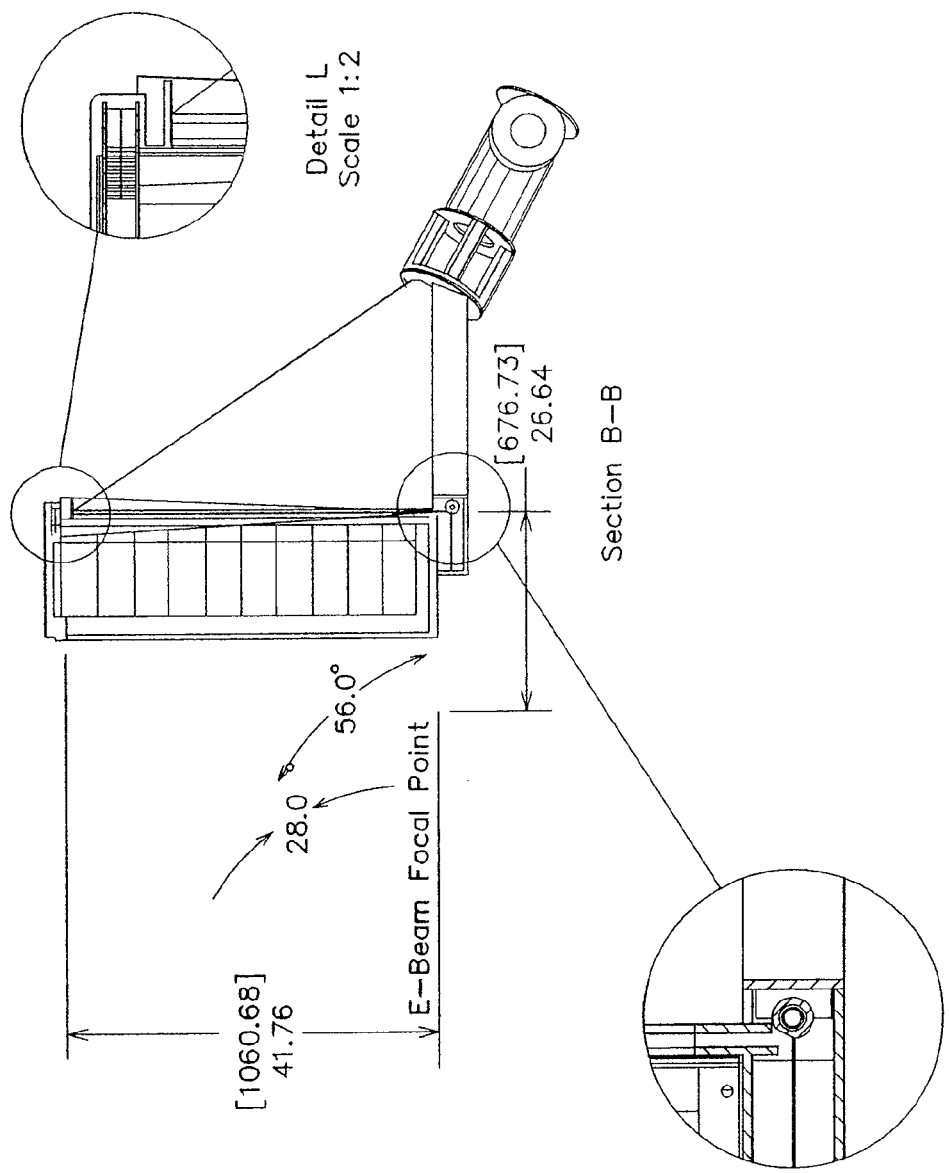
Figure 26A:
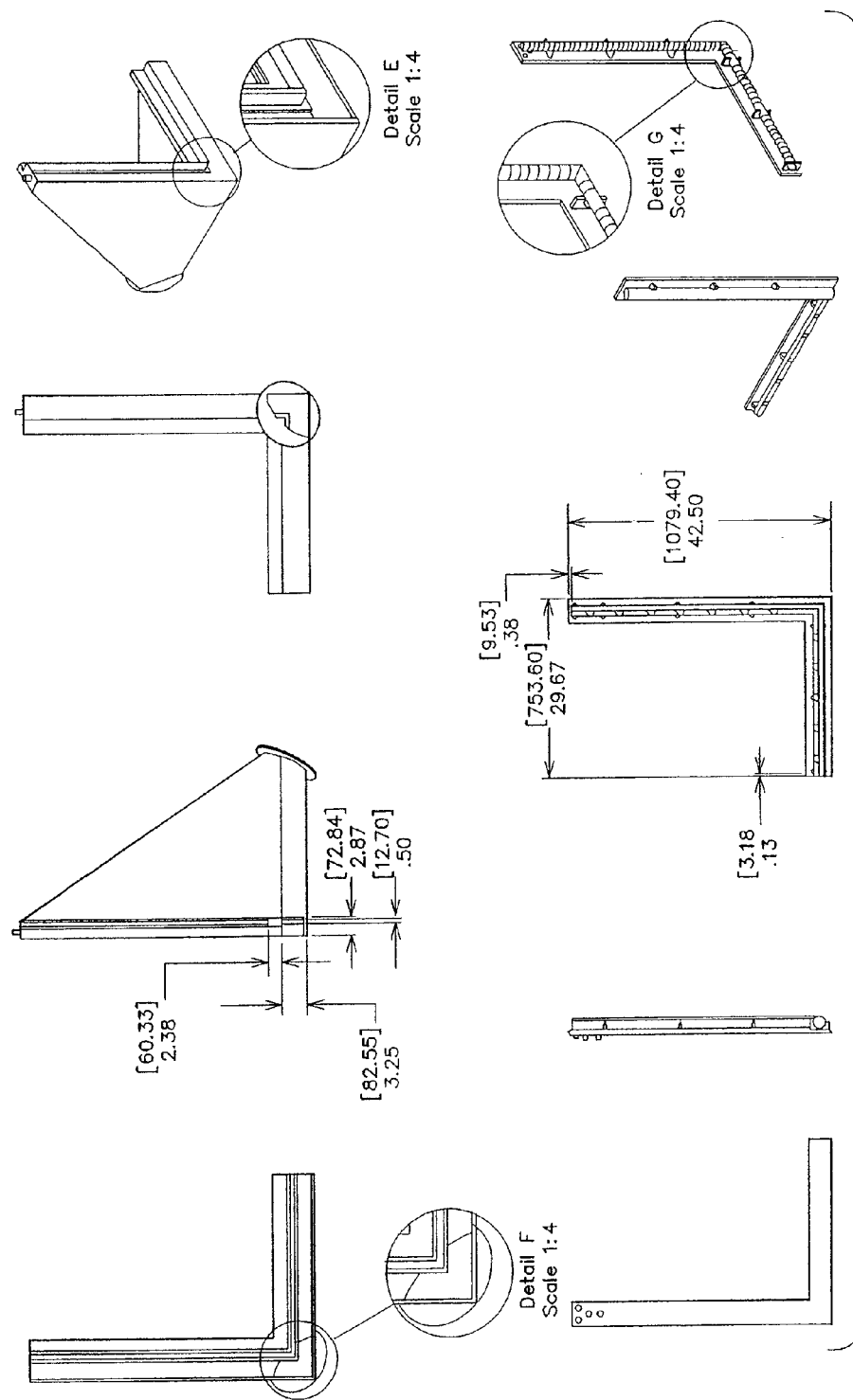
Figure 26B:
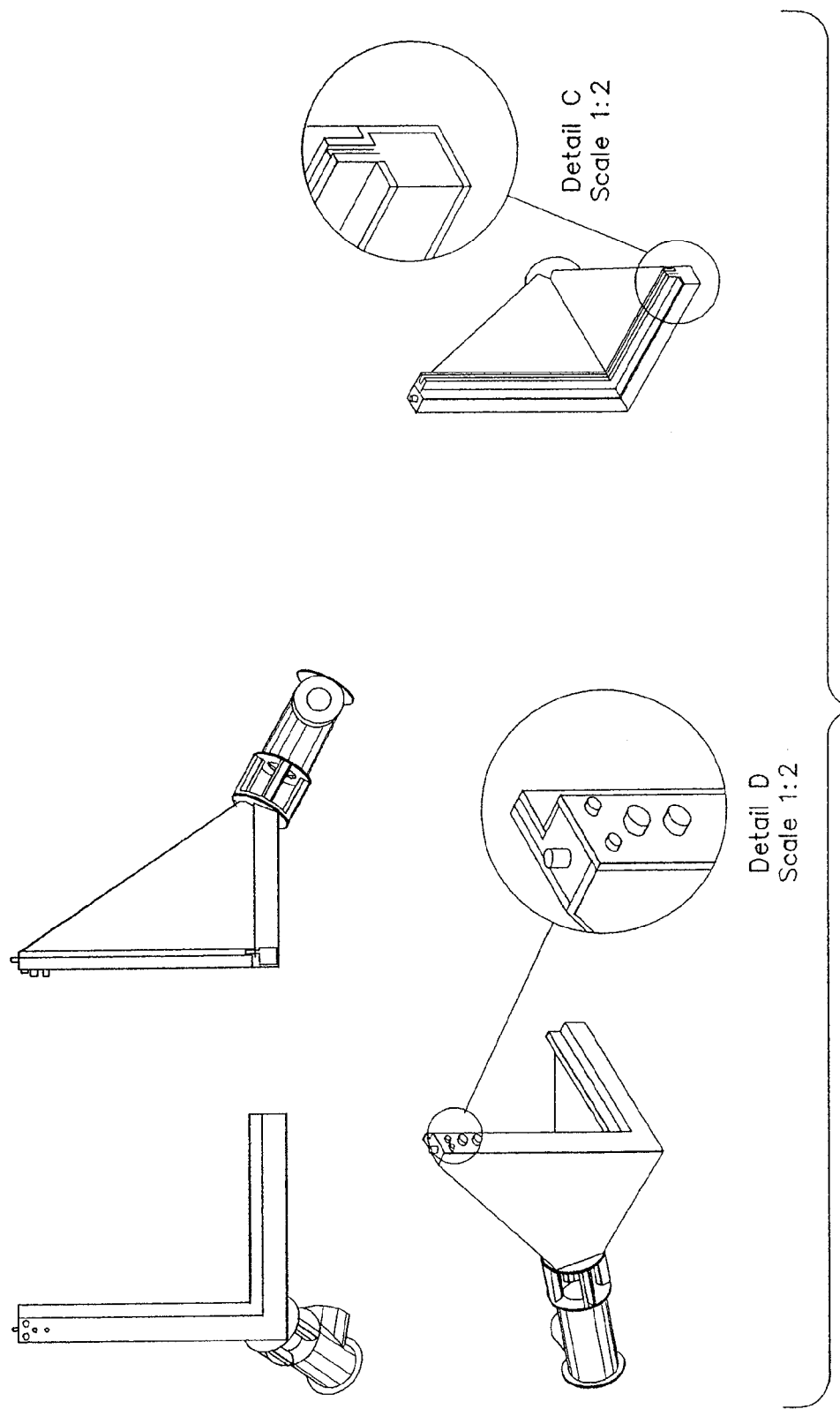
Figure 27A:
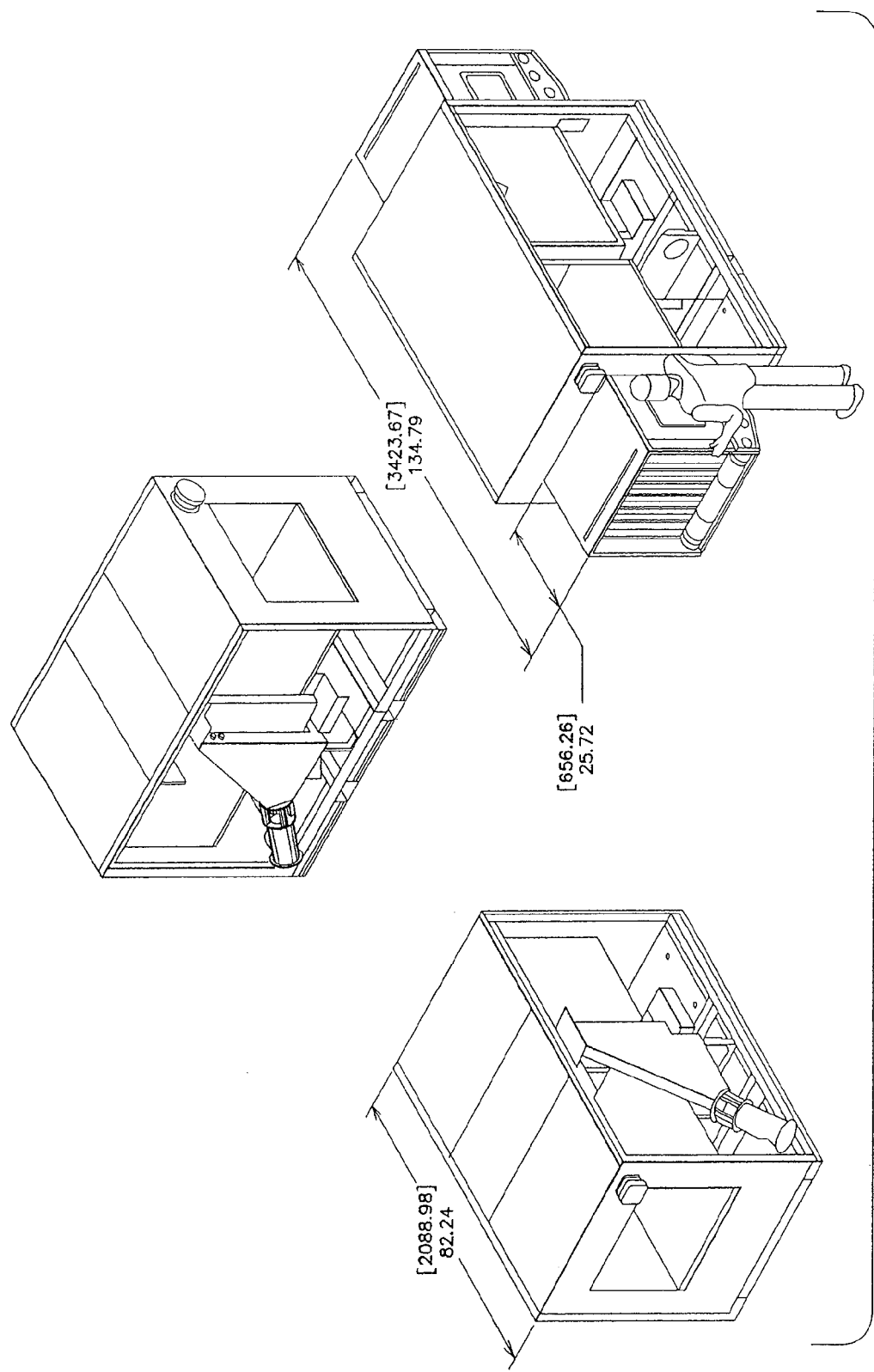
Figure 27B:
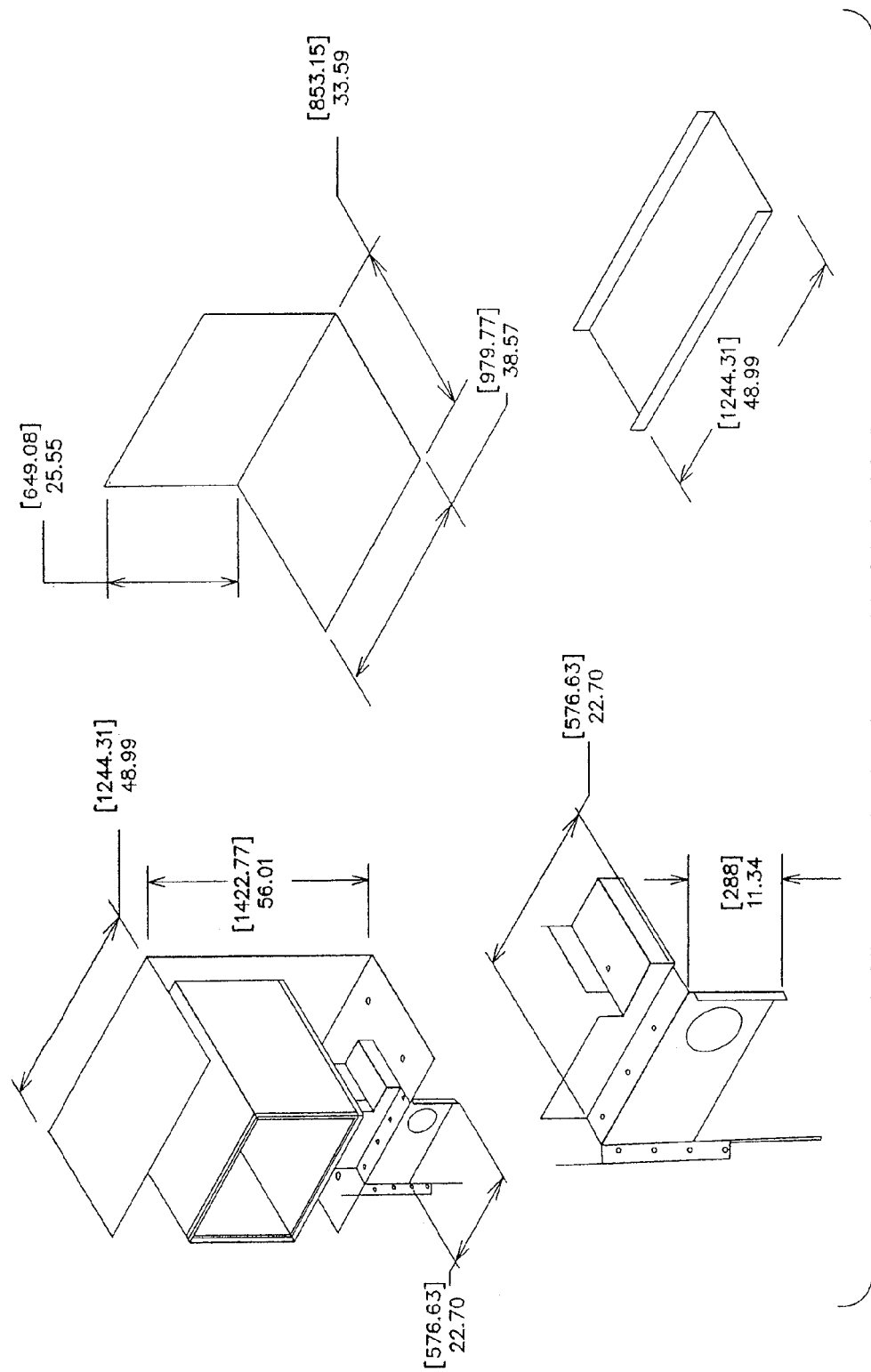

FIGS. 25-27 illustrate various views and details of the X-ray scanning system illustrated in FIG. 24. In particular, FIG. 25 illustrates the front and top views illustrated in FIGS. 24A and 24B, respectively. In addition, FIG. 25 illustrates a side view along section B-B. Various implementation details according to one embodiment of the x-ray scanning system in FIG. 24 are illustrated in the circular magnifications, however, these details place no limitations on the aspects of the invention. FIG. 26 illustrates various exemplary construction details of an e-beam generator with respect to an L-shaped portion of a target for which it is arranged to provide an e-beam.

FIG. 27 illustrates one embodiment of how the various components illustrated in FIGS. 24-26 may be used to construct a x-ray scanning device adapted to inspect object of interest place on a conveyer mechanism that transports the object though a substantially enclosed housing. It should be appreciated that the various construction and implementation details in FIGS. 24-27 are merely exemplary. An x-ray scanning devices may be constructed in any way, as the aspects of the present invention are not limited to any particular type of construction, implementation or arrangement of parts.

It should be appreciated that the embodiments illustrated in FIGS. 24-27 utilize various aspects of asymmetric positioning of e-beam generators. In particular, the e-beam generators in FIG. 24 are arranged asymmetrically with respect to the portions of the targets for which they are respectively intended to scan. FIGS. 24C and 24D further illustrate the positioning of the e-beam generator with respect to the target. FIG. 24D illustrates that the e-beam generator 2450' positioned asymmetrically with respect to both arms of the L-shaped target 2410" portion for which it is configured to scan. In particular, e-beam generator 2450' is positioned asymmetrically with respect to arm 2410*a*' and arm 2410*b*'. As discussed above in connection with FIGS. 30-32, the asymmetric configuration facilitates more compact designs having reduced sweep angle requirements for the e-beam generators.

To energize an e-beam generator, a high voltage power supply may be used to generate the necessary current required by the e-beam generator. In embodiments having multiple e-beam generators, a single high voltage power supply may be shared by the multiple guns to reduce the cost and size of the X-ray scanning system. Applicant has recognized that when two e-beam generators are employed in succession, a shared high voltage power supply conventionally must transition from providing a relatively large current to providing no current to one gun, and must transition from providing no current to providing a relatively large current to the other gun in a relatively short amount of time.

For example, the high voltage power supply may have to transition from providing approximately 40 mA (approximately 6.4 kW of power, or a change of 500 volts) to 0 mA on one gun and from 0 mA to approximately 40 mA on the other gun in a span of approximately 120 μSec. That is, the high voltage supply must be stepped down and stepped up in a very short time frame. This places an extreme dynamic load challenge on the high voltage power supply. In particular, not only is the high voltage supply required to charge and discharge substantially as a step function, but the current provided to the guns must settle out quickly to avoid impacting the quality of the x-rays produced that, in turn, may cause artifacts in the resulting x-ray images.

Applicant has appreciated that by simultaneously de-energizing one gun while energizing another, the power differential the high voltage supply undergoes can be reduced and/or eliminated. For example, as the first gun approaches the end of the portion of the target for which it is adapted to provide an e-beam (e.g., portion 2410*a* in FIG. 24), the high voltage power supply may begin ramping down the current providing to the first gun. At the same time, the high voltage power supply may begin ramping up the current provided to the second gun. In this way, the high voltage power supply avoids having to handle the relatively large load changes resulting from relatively large and substantially instantaneous current changes.

Figure 28:
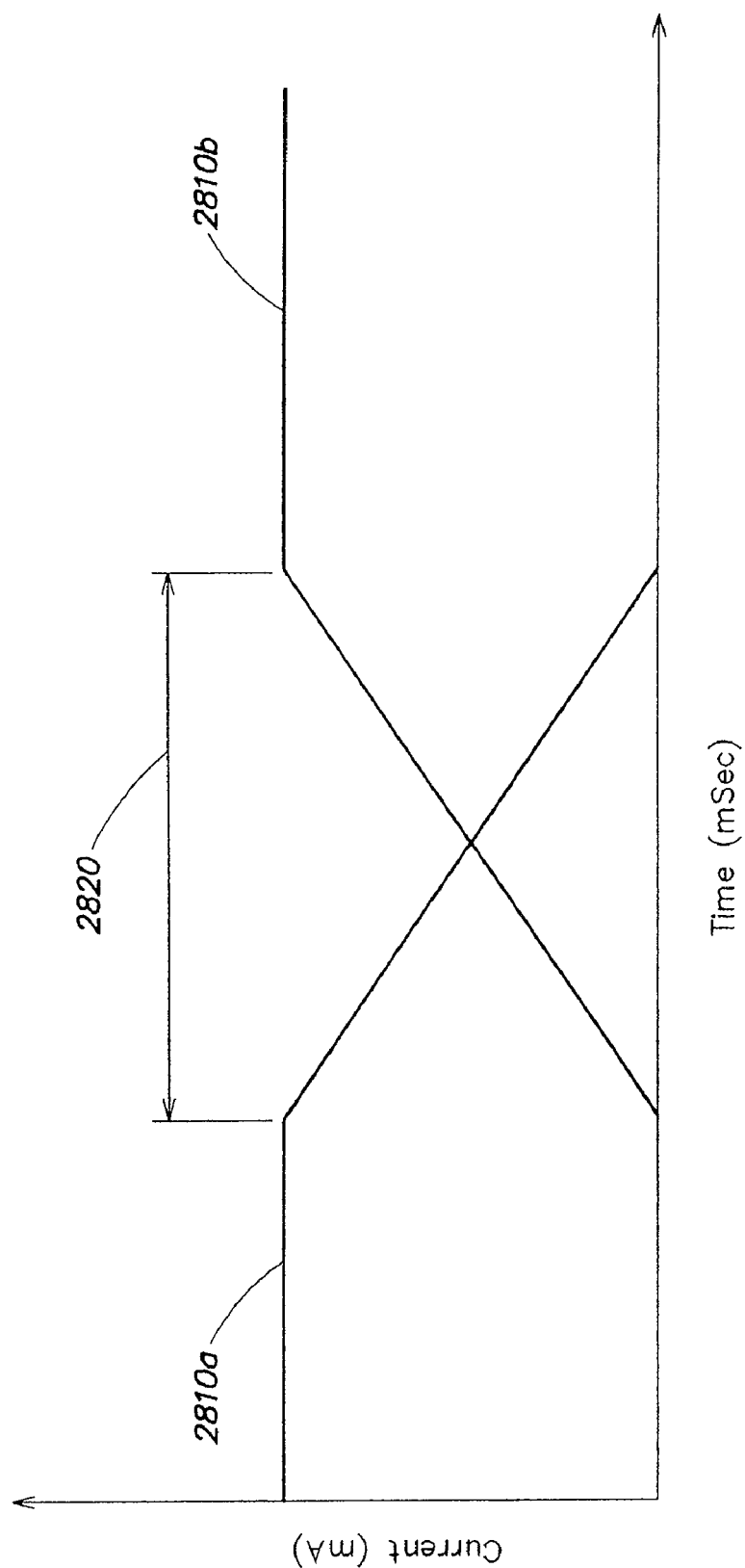
FIG. 28 illustrates a simultaneous energizing and de-energizing schedule for a power supply adapted to provide power to a pair of electron beam generators, in accordance with one embodiment of the present invention.

FIG. 28 illustrates a current transition performed by a high voltage power supply, in accordance with one embodiment of the present invention. The plot in FIG. 28 shows the current provided to a first gun by curve 2810*a* during an interval near the end of the scanning path of the first gun, and the current provided to a second gun by curve 2810*b* near the beginning of the scanning path of the second gun. The transition period 2820 shows the interval in which the first gun is de-energized and the second gun is energized.

As shown, the current provided to the first gun ramps down in a substantially linear fashion. Simultaneously, the current provided to the second gun ramps up according to the same substantially linear function. As a result of the simultaneous charge and discharge of the two guns, the sum of the currents provided remains the same. Accordingly, the load seen by the high voltage power supply doesn't change substantially and the high voltage power supply may be relieved of having to handle extreme dynamic changes in the load environment. Co-transitioning the energizing and de-energizing of the electron guns serves at least two beneficial purpose. First, the generally symmetric and simultaneously charging and discharging tend to cancel each other out to reduce or eliminate large net changes in current that the power supply must generate. Second, because large changes in current are not required, transients in the current generated by rapid transitions may be reduced and/or eliminated. Thus concerns over whether the waveform has settled may be substantially alleviated.

It should be appreciated that the current waveform illustrated in FIG. 28 are merely exemplary and schematic. For example, during the transition period, the currents need not be provided according to a linear waveform, as the currents may be transitioned according to other waveforms such as an exponential transition, near linear transitions, or other curves suitable for transitioning the current in a substantially continuous fashion. Any simultaneous waveforms that reduces the dynamic load change on the high voltage power supply may be used, as the aspects of the invention are not limited in this respect.

In one embodiment, the transition interval during which one gun is energized and the other gun is de-energized occurs while the guns are providing respective e-beams in regions where no target exists such that no X-rays are generated during the transition interval. For example, there may be a gap in the target in a region where current is transitioned off for a first gun and on for a second gun. In this way, no X-ray energy is released during the transition and the detectors will register substantially little if any X-ray radiation. Other methods may be used to prevent X-rays from being generated during the transition period between energizing/de-energizing multiple guns in embodiments where multiple guns are present, as the aspects of the invention are not limited in this respect. For example, e-beam opaque material may be positioned between the electron gun and the detector array during transition periods.

As discussed above, the e-beam generators are relatively high power devices. For example, an e-beam generator may operate at approximately 6.4 kW of power or more. A substantial amount of this energy is dissipated in heat (largely at the impact point of the e-beam with the target), which, absent measures to disperse this heat, may cause damage to the equipment. Applicant has appreciated that by providing targets with a hollow core, cold water or some other coolant may be circulated through the target to dissipate excess heat. The liquid coolant absorbs heat and carries it out and away from the target and other sensitive components that may be damaged by high temperature resulting from heat dissipation of the energy in the e-beam generators.

In one embodiment, an x-ray detection system has a cooling system coupled to the target having at least one hollow portion. The cooling system may include a pump that circulates a liquid coolant through the at least one hollow portion. The liquid coolant may capture heat generate by the conversion of the e-beam energy to x-ray energy and neutralize and/or transport it away from the target and/or other sensitive components. The cooling system may be arranged any fashion, as the aspects of the invention are not limited for use with any particular type of cooling system.

An e-beam may be sequentially directed along a target to produce X-rays at varying angles about an object being scanned. By moving the point at which the e-beam impinges on the target, a number of views of the object at different angles may be obtained. The detector signals generated in response to impinging X-ray radiation over different viewing angles (e.g., over 180°) may be back-projected or otherwise processed to form a computer tomography (CT) image (or, in some cases, a laminographic image). That is, X-ray data represented as a function of detector location (t) (e.g., distance from the center of the reconstruction) and view angle θ, referred to as view data, may be transformed into image data representing, for example, density as a function of space.

Figure 5:
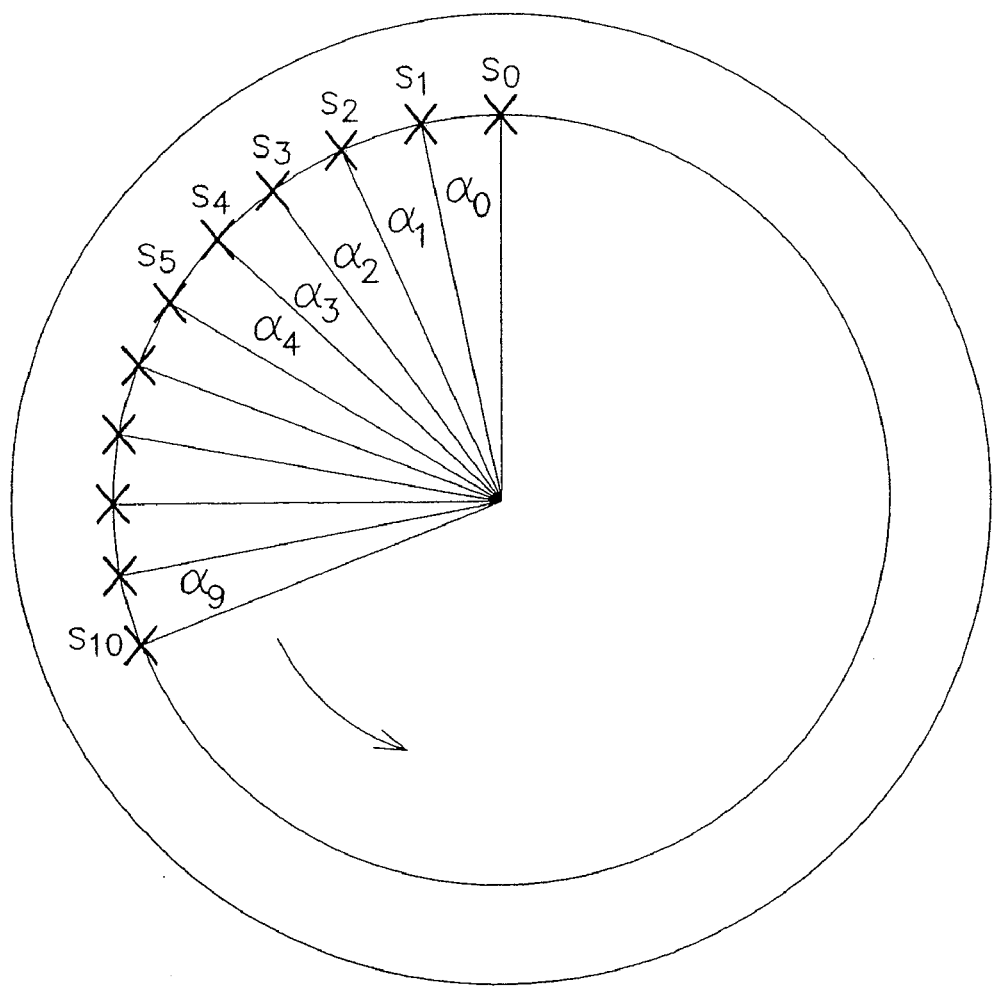
FIG. 5 illustrates equal penetration angles resulting from circular geometry systems.

The process of transforming view data into image data is referred to as image reconstruction and numerous methods of performing the transformation are known in the art. Back-projection, for example, is a well known image reconstruction algorithm. In back-projection, the view data in a (t, θ) coordinate frame is mapped into object or image space in a (x, y) coordinate frame. That is, each location in (x, y) space is assigned an intensity value based on attenuation information contained in the view data. As a general matter, image reconstruction is less complicated when the angle formed between successive locations at which the e-beam impinges on the target (i.e., successive X-ray source locations) and a center point of the inspection region are equidistant. For example, FIG. 5 illustrates a circular target of a conventional X-ray scanning system. In order to generate equal $\alpha_i$, the arc segments between each successive sample point $s_i$ (i.e., where the e-beam impinges on the target) should be made equal. To achieve this, conventional systems direct the e-beam along the circular scanning path at a constant velocity or uniform speed or scan rate, and sample detector outputs at the appropriate sampling rate.

Figure 6:
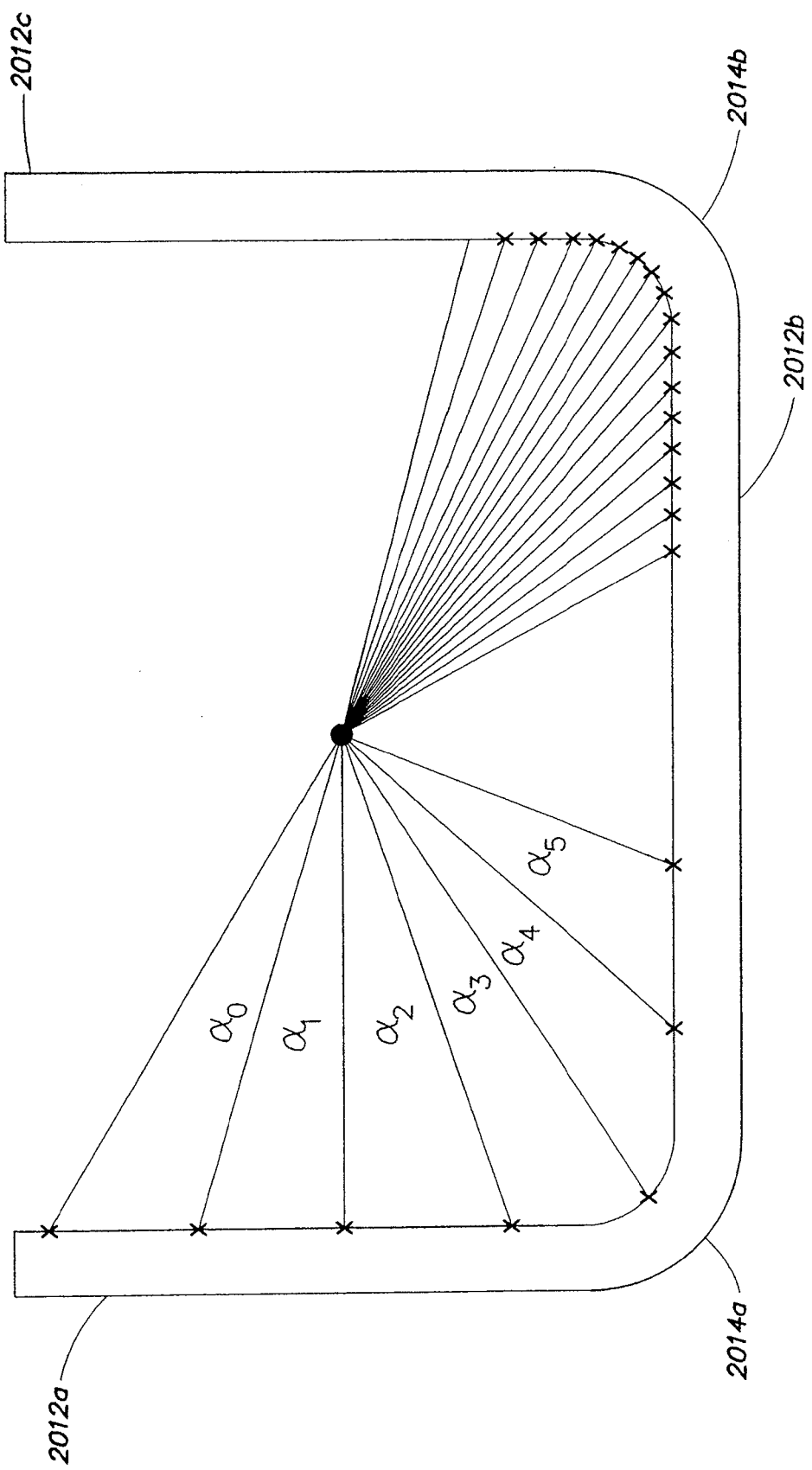
FIG. 6 illustrates unequal penetration angles that result in arbitrary geometry systems, in accordance with one embodiment of the present invention.

However, in arbitrary geometry scanning systems, a constant scanning rate may not result in equidistant penetration angles with respect to a center location of the inspection region. FIG. 6 illustrates the generally U-shaped target of FIGS. 2-4. As shown, a constant scanning speed along the substantially linear arm 2012a will produce equidistant X-ray source locations, but will result in penetration angles that vary depending on where along the scanning path the e-beam is impinging. That is, a constant scan rate will produce variable angles $\alpha_i$ along the scan path. In FIG. 6, the target is sparsely sampled to highlight the differences in penetration angles. It should be appreciated that during operation, the samples will typically be closer together.

When scanning at locations along the circular arc segments of the target (e.g., circular arc segment 20), a constant velocity scan rate will impinge at locations that are not equidistant with respect to penetration angles generated along the linear segments, nor will the penetration angles be equidistant with respect to the linear segments, nor to each other as illustrated by the exemplary samples in the lower right quadrant of the target. The scan path is sampled differently in the low right quadrant to highlight the dissimilarities in penetration angles and sample distances that occur at the transitions between target segments of different geometries.

Accordingly, a constant or uniform scanning rate in non-circular geometries may make image reconstruction more complicated. Applicant has appreciated that scanning an e-beam along a scanning path of a non-circular geometry, wherein the scanning is performed at a non-constant and/or non-uniform velocity (i.e., a non-uniform scan rate), equidistant penetration angles may be produced. Any variable rate scanning path may be chosen, for example, the scan rate may be varied as a function of the location along the scanning path. In one embodiment, the scanning rate is varied along the scanning path such that penetration angles generated along the scanning path are approximately equal, thus simplifying image reconstruction computations. It should be appreciated that the scanning rate schedule may depend on the shape of the target. A target geometry of all linear segments may have a different scanning rate schedule than a detector geometry having a combination of linear and circular arc segments.

Figure 7:
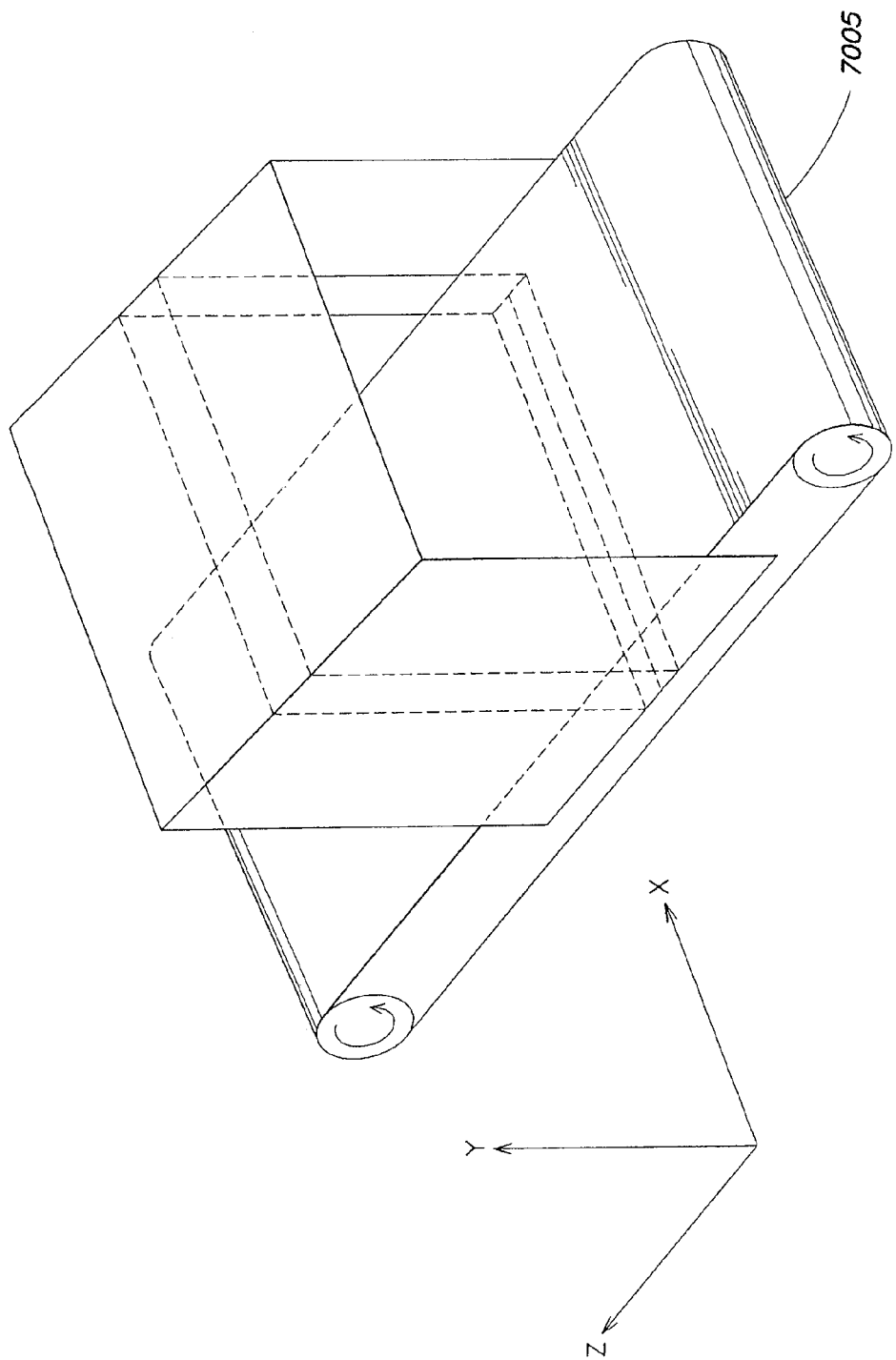
FIG. 7 illustrates an arbitrary geometry system with a conveyer system to convey objects through a covered tunnel, in accordance with one embodiment of the present invention.
Figure 8:
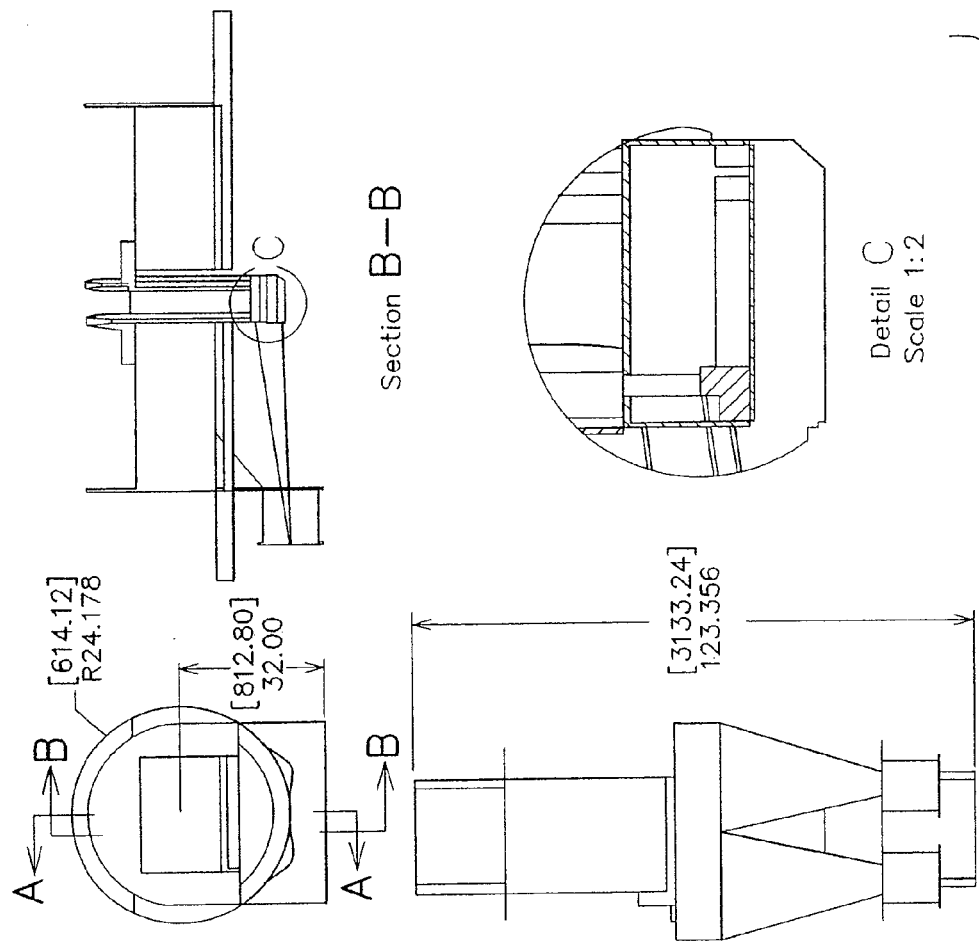
Figure 9:
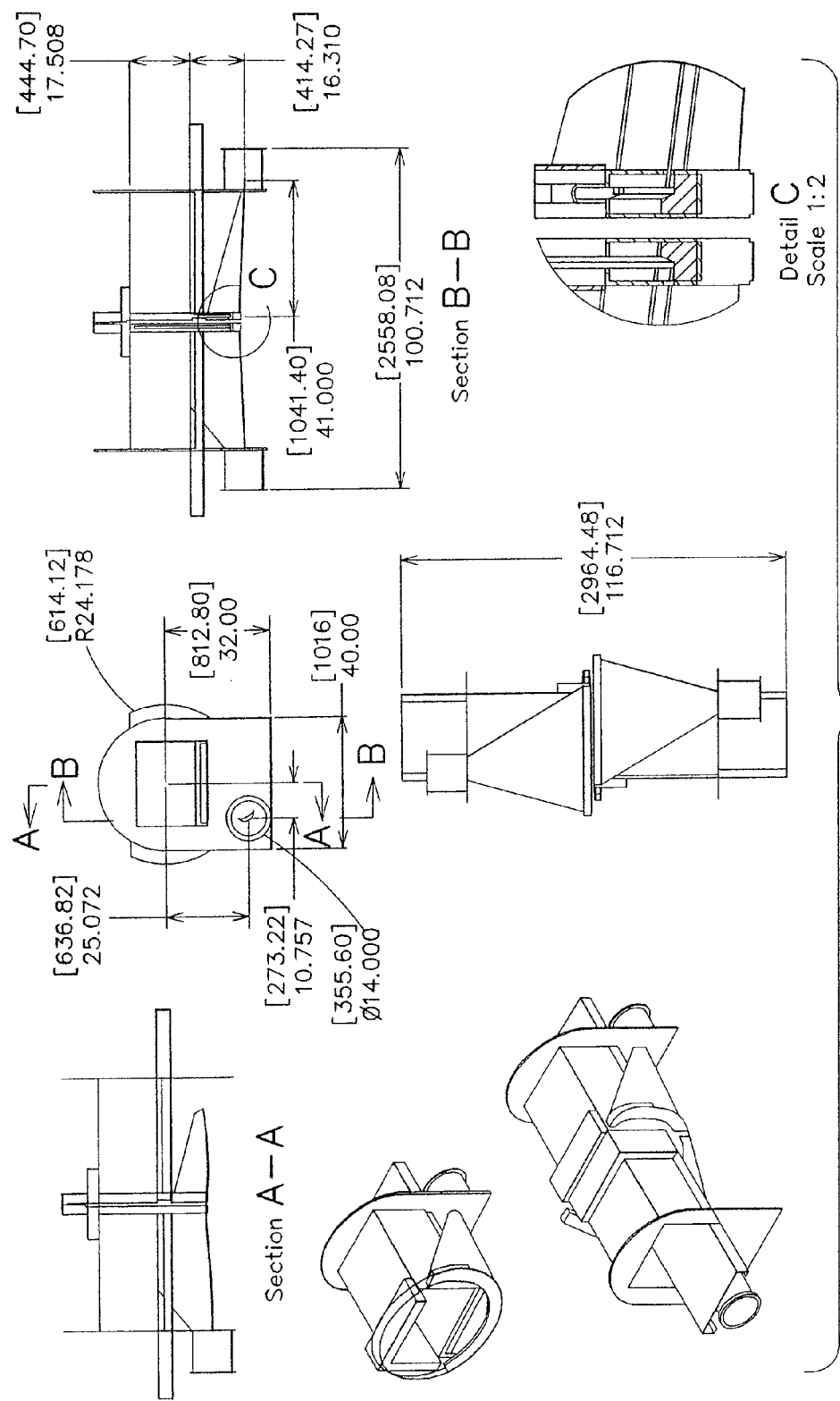
Figure 10:
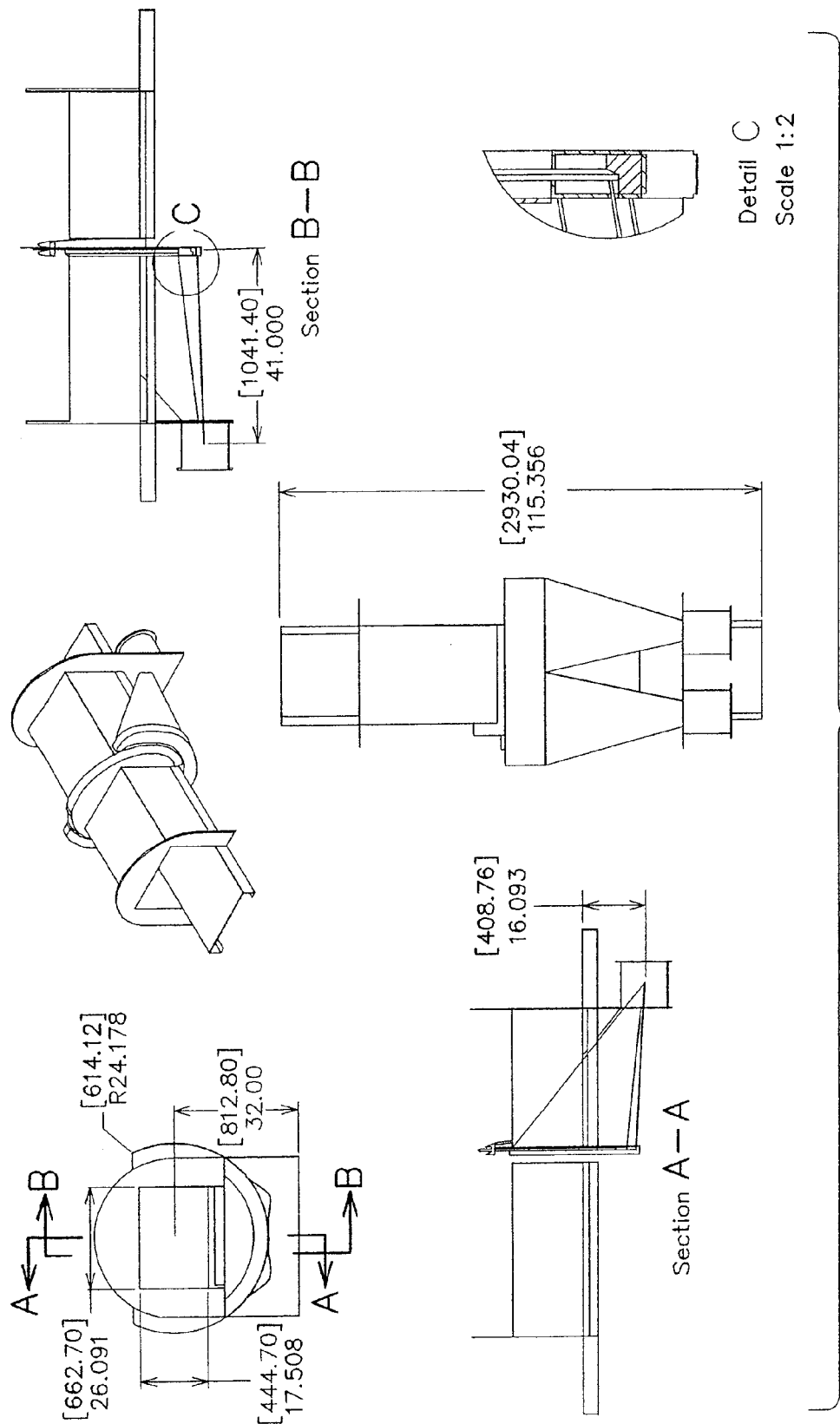
Figure 11:
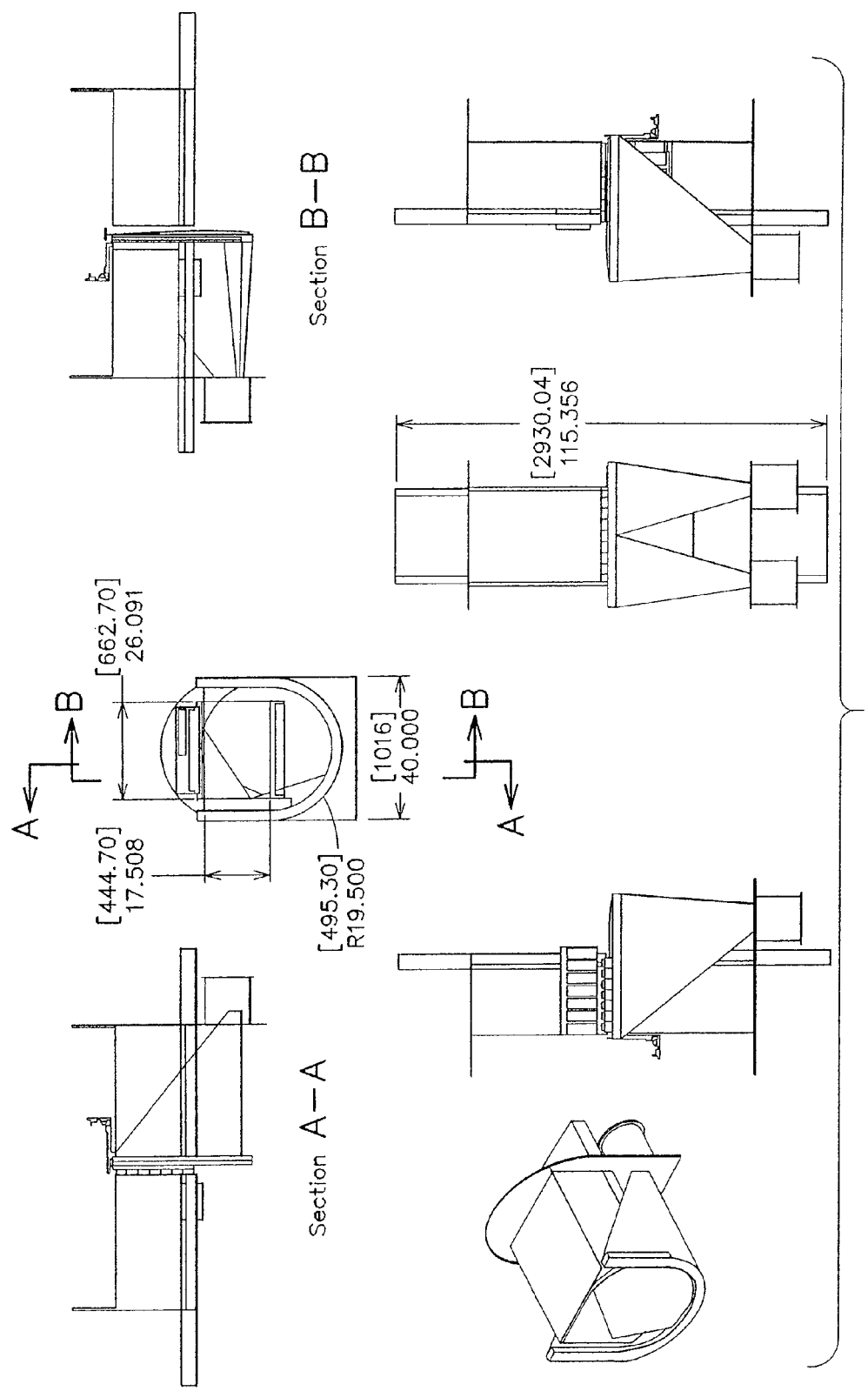
Figure 12:
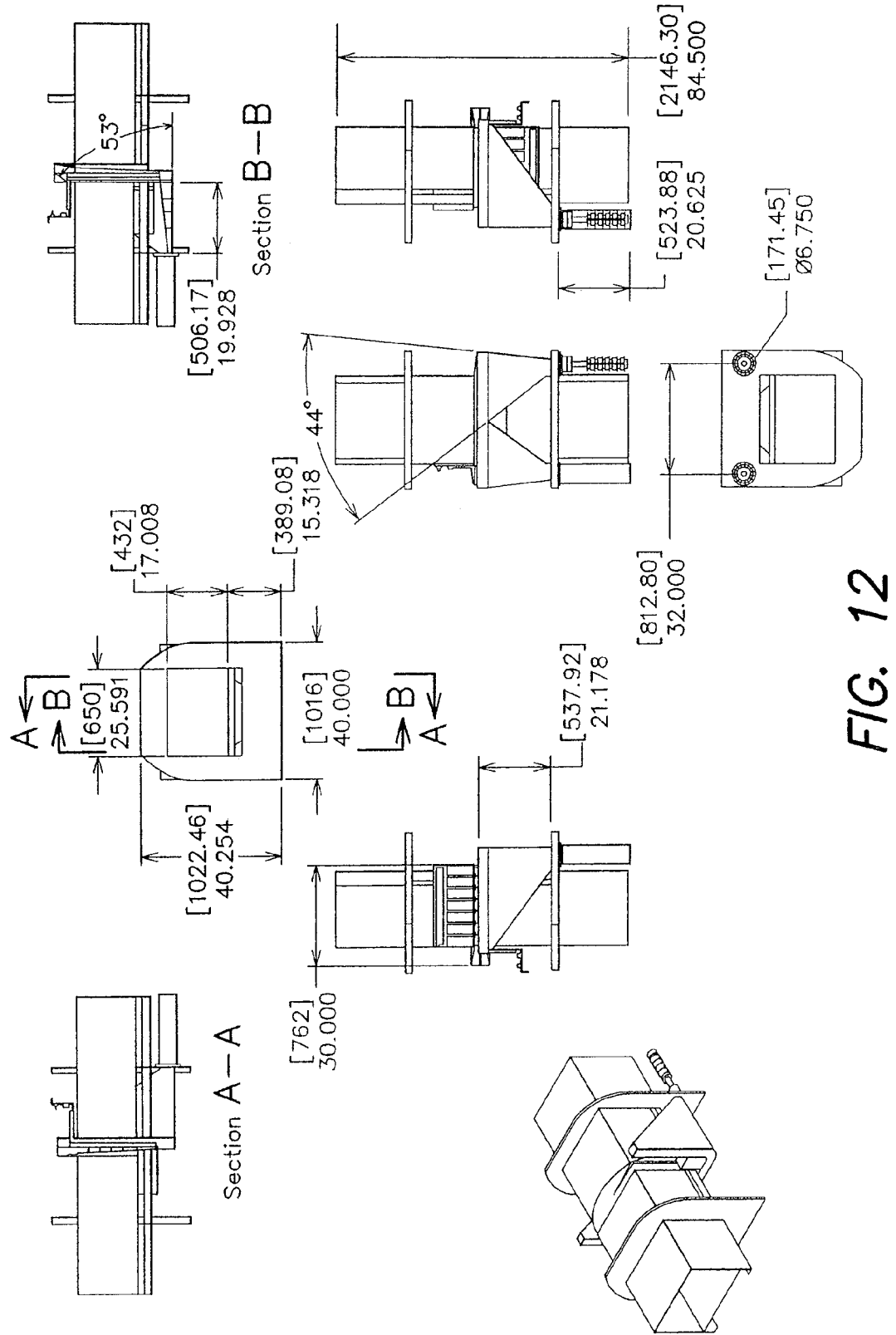
Figure 13:
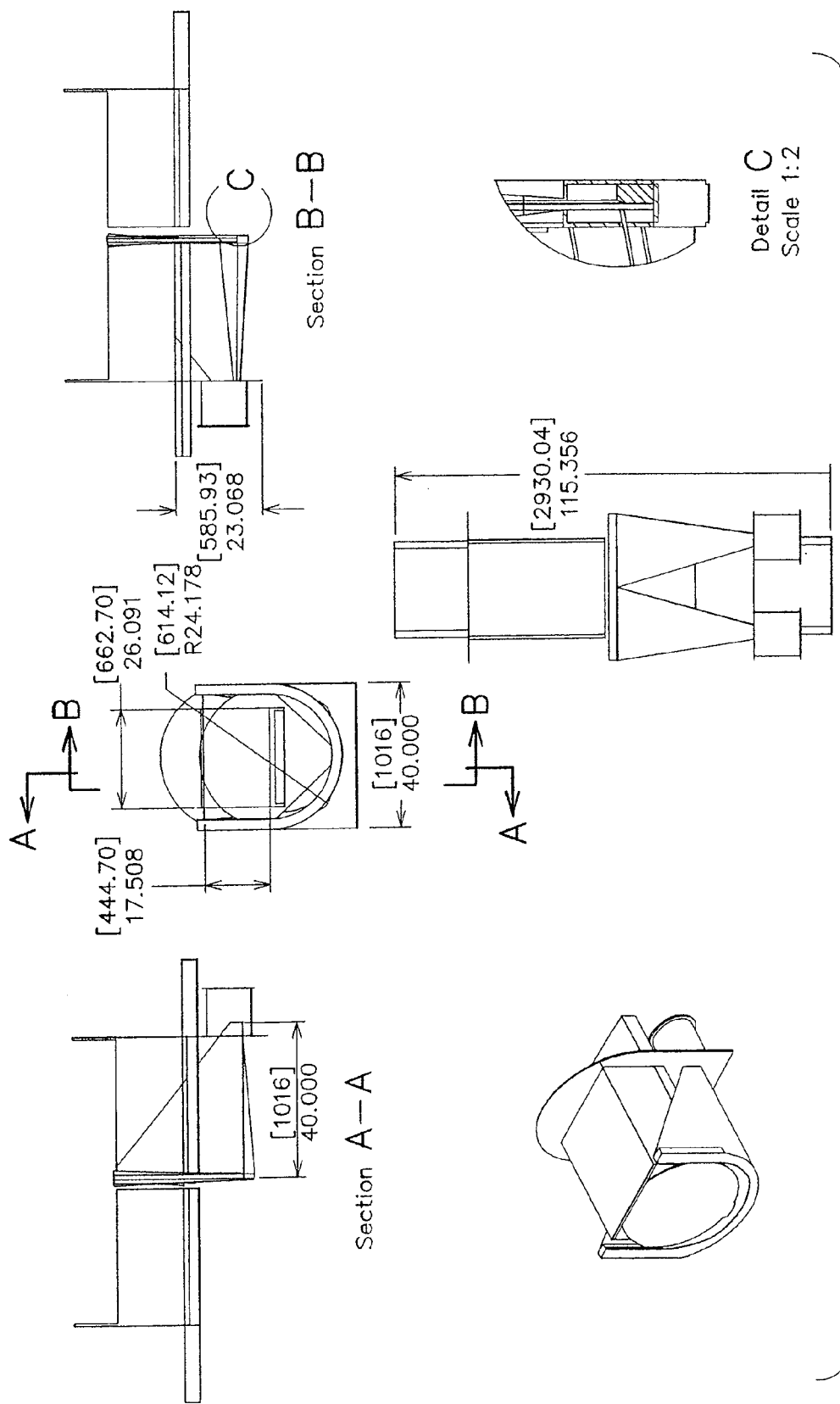
Figure 23:
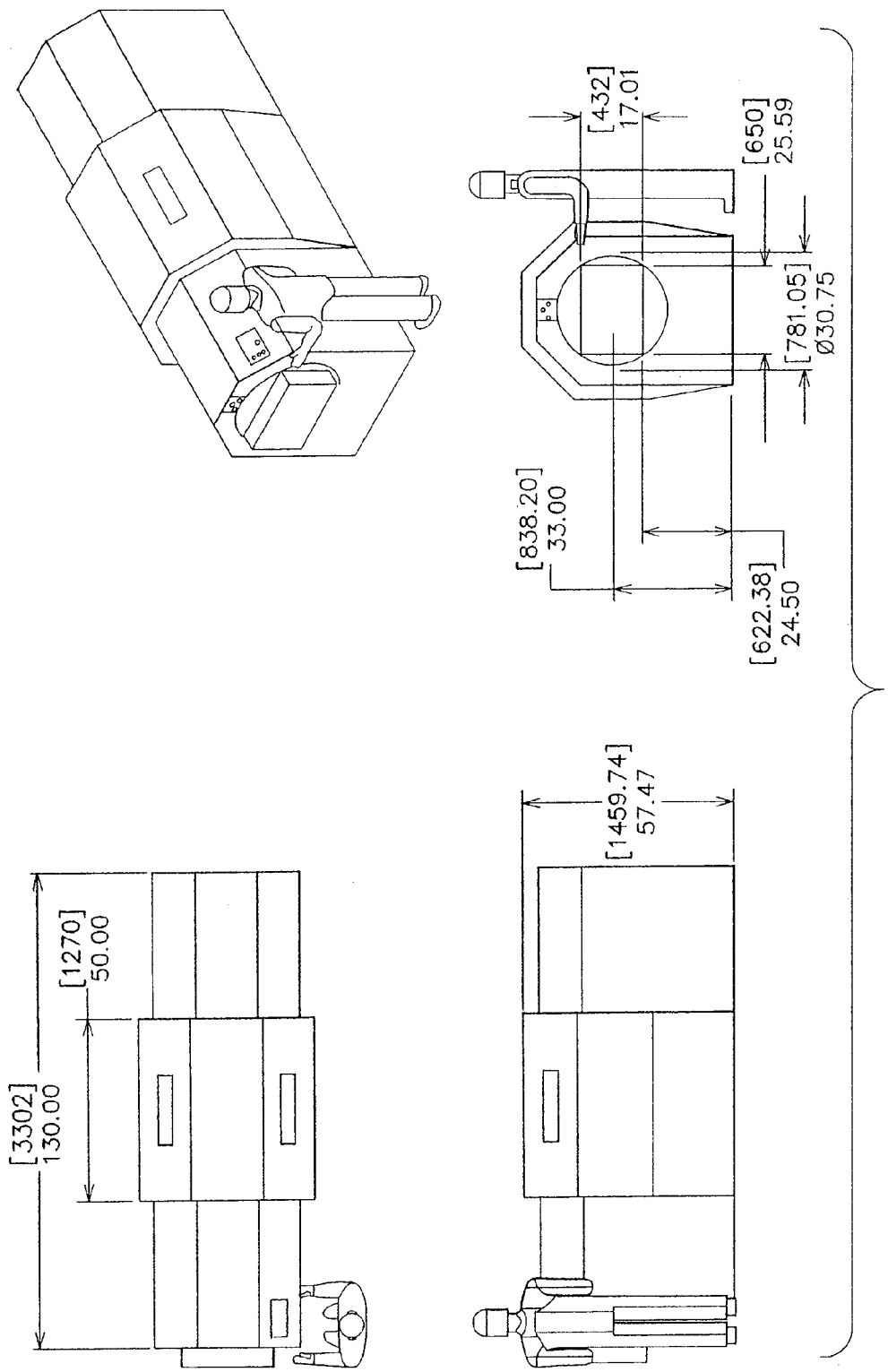

In many X-ray scanning systems, such as X-ray detection systems adapted for scanning items such as articles of baggage, parcels, or other containers, where it is desired to perform an inspection of the item for prohibited material, the items being inspected may be conveyed through an inspection region on a conveyor. For example, FIG. 7 illustrates an X-ray detection system where items for inspection are carried through a detection area on a conveyor 7005 in a direction parallel to the z-axis. FIGS. 23 and 27 illustrate other embodiments of X-ray detection systems wherein items to be inspected are conveyed through a tunnel to be exposed to X-ray radiation. Synchronizing of the scan and the position of the conveyer facilitates pipelining the reconstruction into a regular grid of voxel dimensions.

It may be desirable to synchronize the scanning rate with the speed of the conveyor. In this way, as the e-beam traces along the scan path, the X-rays produced by the target will penetrate the object of interest at substantially the same cross-section. That is, X-rays penetrating the object at the various angles about the object will carry attenuation information about substantially the same plane through the object. In conventional circular geometry scanning systems, by appropriately selecting the constant velocity by which the target is scanned, the scanning may be synchronized with the conveying apparatus. It should be appreciated that with the motion in the z-direction, the circular scanning path becomes a circular helix or corkscrew shape. The '271 patent incorporated above describes the conventional understanding of the criticality of a constant scan rate to synchronize multi-size scanning in circular geometry systems.

However, a constant scanning path along a non-circular scanning path frustrates synchronization with the scanning apparatus. Accordingly, Applicant has appreciated that providing a variable scanning rate in an arbitrary geometry (i.e., non-circular geometry) scanning system may facilitate synchronization with the conveyance system such that the X-rays generated from one traversal of the scanning path penetrates the object being scanned at substantially the same plane, slice or cross-section.

The schedule at which the scan rate is varied to synchronize the scanning with the conveying apparatus may depend on a given geometry of the target and whether the target is continuous or provided in discontinuous segments offset in the direction of conveyance. It should be appreciated that any desired scan rate schedule may be used, as the aspects of the invention are not limited in this respect. In addition, the scan rate schedule may be generated to produce equal penetration angles, to synchronize the system or both.

It should be appreciated that an X-ray scanning system may include more than one target and/or detector array. For example, in some embodiments, multiple detector arrays are disposed successively in the direction of motion of an item being inspected. One or more targets may be positioned to generate X-rays to impinge on the multiple detector arrays. In one embodiment, each detector array has a respective target positioned to generated X-rays to impinge on the detector array. Any configuration and combination of target and detector array may be used, as the aspects of the invention are not limited in this respect.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. In particular, the various aspects of the invention are not limited for use with any particular type of X-ray scanning device. The aspects of the invention may be used alone or in any combination and are not limited to the combinations illustrated in the embodiments of the foregoing.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. An x-ray scanning device comprising:
   at least one target adapted to convert electron beam (e-beam) energy into x-ray energy, the at least one target arranged to provide at least some of the x-ray energy through an inspection region, the inspection region including an imaging plane wherein a cross-section of an object being scanned is exposed to the x-ray energy;
   at least one array of detectors adapted to detect x-ray radiation emitted from the at least one target and passing through the inspection region;
   a first e-beam source and a second e-beam source, each configured to generate e-beam energy and arranged to generate a first e-beam and a second e-beam, respectively, in a direction substantially perpendicular to the imaging plane;
   a vacuum tube coupled to both the first e-beam source and the second e-beam source in which the first e-beam and the second e-beam pass; and
   at least one first deflector arranged to deflect the first e-beam and at least one second deflector arranged to deflect the second e-beam generated by the first e-beam source and the second e-beam source, respectively, to impinge on the at least one target.

2. The x-ray scanning device of claim 1, wherein the at least one array of detectors includes a substantially circular detector array.

3. The x-ray scanning device of claim 2, wherein the at least one target includes a first substantially circular portion positioned substantially diametric to the substantially circular detector array.

4. The x-ray scanning device of claim 3, wherein the circular detector array is offset from the first substantially circular portion in a direction substantially perpendicular to the imaging plane.

5. The x-ray scanning device of claim 1, wherein the at least one detector array includes a first substantially linear detector array and a second substantially linear detector array, the first substantially linear detector array and the second substantially linear detector array being arranged substantially perpendicular to each other to form a substantially L-shaped detector array.

6. The x-ray scanning device of claim 1, wherein the at least one target and the at least one array of detectors are offset with respect to one another in a first direction substantially perpendicular to the imaging plane.

7. The x-ray scanning device of claim 6, wherein the at least one array of detectors includes a first detector array offset from the at least one target in the first direction and a second detector array offset from the at least one target in a second direction, the second direction being substantially opposite to the first direction.

8. The x-ray scanning device of claim 7, wherein the first detector array includes a first substantially linear detector array and a second substantially linear detector array, the first substantially linear detector array and the second substantially linear detector array being arranged substantially perpendicular to each other, and wherein the second detector array includes a third substantially linear detector array and a fourth substantially linear detector array, the third substantially linear detector array and the fourth substantially linear detector array being arranged substantially perpendicular to each other.

9. The x-ray scanning device of claim 8, wherein the first substantially linear detector array and the second substantially linear detector array form a first substantially L-shaped detector array and the third substantially linear detector array and the fourth substantially linear detector array form a second substantially L-shaped detector array, the first L-shaped detector array and the second L-shaped detector array being positioned substantially diametric to each other.

10. The x-ray scanning device of claim 6, further comprising a conveyor mechanism adapted to convey objects through the imaging plane, and wherein the at least one target and the at least one array of detectors are offset with respect to one another substantially in the direction in which the conveyor mechanism conveys the objects through the imaging plane.

11. The x-ray scanning device of claim 1, wherein the at least one target includes a first portion and a second portion and the first e-beam source is arranged to provide first e-beam energy to the first portion and the second e-beam source is arranged to provide second e-beam energy to the second portion.

12. The x-ray scanning device of claim 11, wherein the at least one first deflector directs the first e-beam to the at least one target along a first scanning path over the first portion of the at least one target and the at least one second deflector directs the second e-beam to the at least one target along a second scanning path over the second portion of the at least one target.

13. The x-ray scanning device of claim 12, wherein the at least one target includes a third portion that includes part of the first portion and part of the second portion such that the first scanning path and the second scanning path overlap along the third portion.

14. The x-ray scanning device of claim 1, wherein the at least one first deflector is positioned to deflect the first e-beam and the at least one second deflector is positioned to deflect the second e-beam, respectively, substantially at a single location along the trajectory of the first e-beam and the second e-beam.

15. The x-ray scanning device of claim 1, wherein the at least one first deflector bends the first e-beam and the at least one second deflector bends the second e-beam, respectively, from the direction substantially perpendicular to the imaging plane towards a plane parallel with the imaging plane.

16. The x-ray scanning device of claim 1, wherein the least one first deflector deflects the first e-beam to impinge on a first portion of the target and the at least one second deflector deflects the second e-beam to impinge on a second portion of the target.

17. The x-ray scanning device of claim 16, wherein the at least one target includes a third portion that includes part of the first portion and part of the second portion such that the first portion and the second portion overlap at least within the third portion.

* * * * *